United States Patent [19]

McAlpine et al.

[11] Patent Number: 4,918,174
[45] Date of Patent: Apr. 17, 1990

[54] TIACUMICIN COMPOUNDS

[75] Inventors: James B. McAlpine, Libertyville; Marianna Jackson, Waukegan; James Karwowski, Mundelein, all of Ill.

[73] Assignee: Abbott Laboratories, Abbott Park, Ill.

[21] Appl. No.: 912,438

[22] Filed: Sep. 26, 1986

[51] Int. Cl.$^4$ .................... A61K 31/70; C07D 313/00; C07D 407/00; C07D 493/00
[52] U.S. Cl. ........................... 536/7.1; 536/1.1; 536/16.8; 549/346
[58] Field of Search ................ 549/346; 536/7.1, 16.8, 536/1.1; 514/23

[56] References Cited

U.S. PATENT DOCUMENTS

| | | | |
|---|---|---|---|
| 3,978,211 | 8/1976 | Coronelli et al. | 424/120 |
| 4,026,766 | 5/1977 | Tomita et al. | 435/70 |
| 4,081,532 | 3/1978 | Celmer et al. | 435/911 |
| 4,202,968 | 5/1980 | Tamura et al. | 536/16.8 |
| 4,242,327 | 12/1980 | Ohba et al. | 536/16.8 |
| 4,293,490 | 10/1981 | Abbott et al. | 435/71 |
| 4,302,450 | 11/1981 | Comai et al. | 514/451 |
| 4,746,511 | 5/1988 | Kobatake et al. | 536/1.1 |

FOREIGN PATENT DOCUMENTS 61-173785 8/1986 Japan.

OTHER PUBLICATIONS

Coronelli et al., J. of Antibiotics, 28 (4) 253–259, (Apr. 1975).
Sergio et al., J. of Antibiotics, 28 (7), 543–549, (Jul. 1975).
Martinelli et al., J. of Antibiotics, 36 (10), 1313–1323, (Oct. 1983).
Parenti et al., J. of Antibiotics, 28 (4), 247–252, (Apr. 1975).
Omura et al., J. of Antibiotics, 39(10), 1407–1412, (Oct. 1986).
Arnone et al., J. Chem. Soc. Perkin Trans I, 1353–1359, (1987).
Cavalleri et al., J. of Antibiotics, 41(3), 308–315, (Mar. 1988).
Kinashi et al., "Structure of Concanamycin A", Tetrahedron Letters, vol. 22, No. 39, pp. 3861–3864, 1981.
Kinashi et al., "Isolation Characterization of Concanamycins A, B, and C", The Journal of Antibiotics, vol. 37, No. 11, pp. 1333–1343 (1984).
Kinashi et al., "Alkaline Degradation Products of Concanamycin A", Tetrahedron Letters, vol. 22, No. 39, pp. 3857–3860, 1981.
Omura et al., "AM-2604 A, a New Antiviral Antibiotic Produced by a Strain of *Streptomyces*", The Journal of Antibiotics, pp. 1632–1637, 1982.
Anderton et al., "Some Structural Features of Borrelidin, an Antiviral Antibiotic".
Buck et al., "The Anti-Borrelia Effect of Borrelidin", Transactions of the New York Academy of Sciences, pp. 207–211, (1949).
Hirakawa et al., "Effect of the Antibiotic, Borrelidin, on the Production of L-Threonine by *E. coli* Auxotrophs", Agr. Biol. Chem. 38(1), 85–89, 1974.
Nass et al., "The Effect of the Antibiotic, Borrelidin, on the Regulation of Threonine Biosynthetic Enzymes and *E. coli*", Biochemical and Biophysical Research Communications, vol. 34, No. 1, 1969.
Hutter et al., "Stoffwechselproduckte von Mikroorganismen", Biochemische Zeitschrift 344, 190–196 (1966).
Keller-Schierlein, "Uber die Konstitution des Borrelidins", vol. 50, Fasciculus 3 (1967), No. 75–76, pp. 731–753.

*Primary Examiner*—Ronald W. Griffin
*Attorney, Agent, or Firm*—Andreas M. Danckers; Martin L. Katz

[57] ABSTRACT

New compounds, tiacumicins, are produced by a microorganism belonging to the genus *Dactylosporangium*. The compounds are effective Gram-positive antibiotics.

12 Claims, 18 Drawing Sheets

FIGURE 1. TIACUMICIN A ULTRAVIOLET SPECTRUM
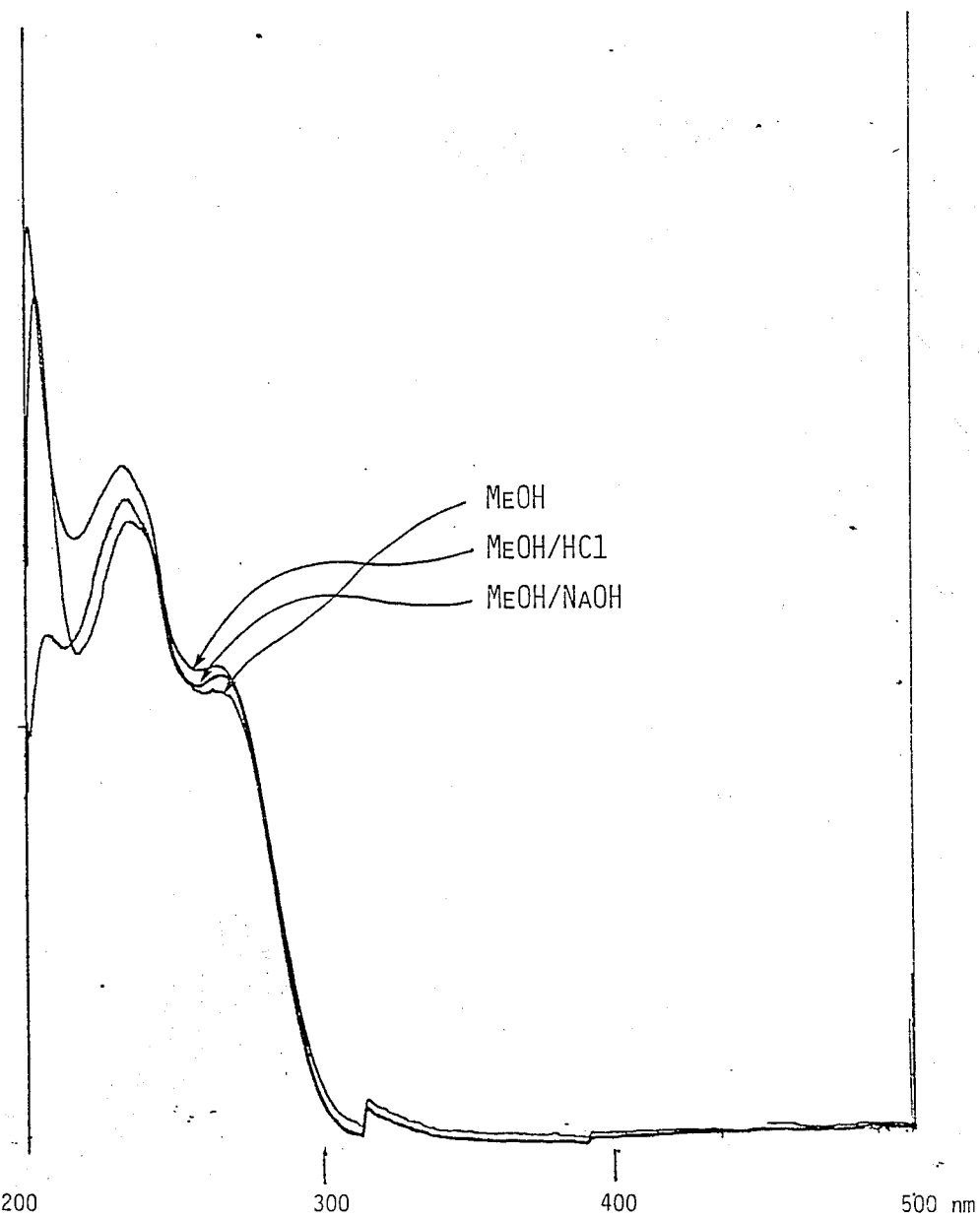

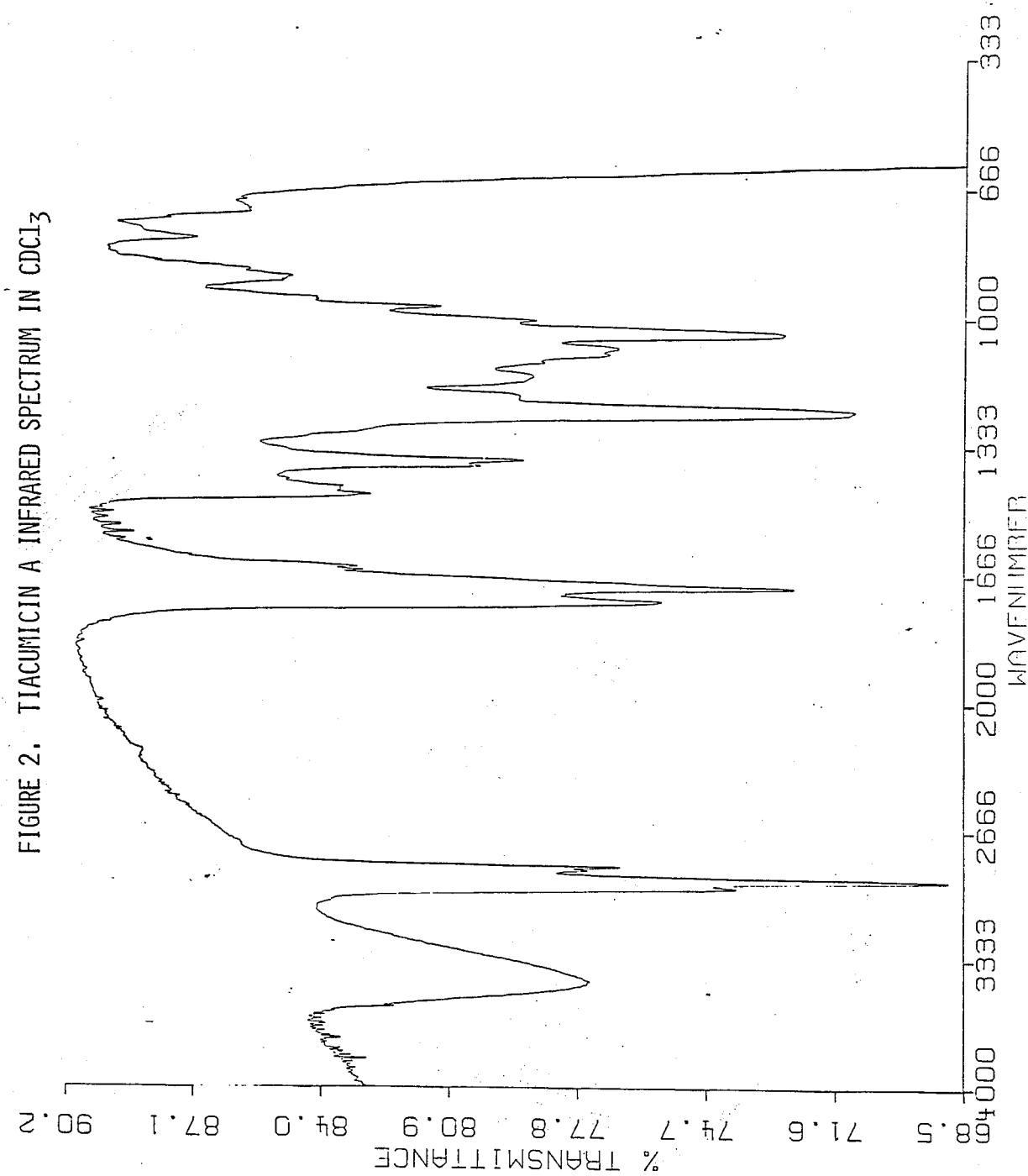
FIGURE 2. TIACUMICIN A INFRARED SPECTRUM IN CDCl₃

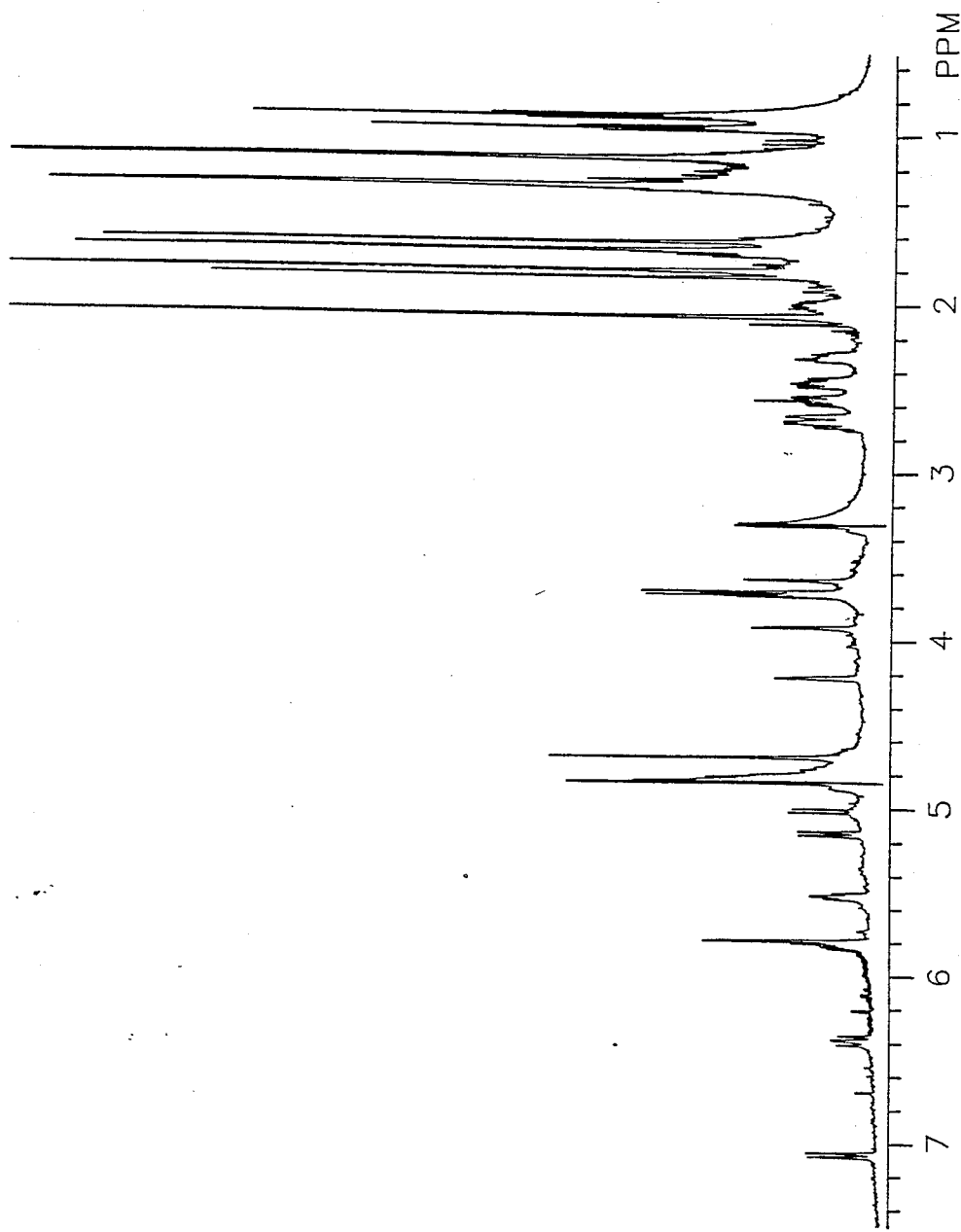
FIGURE 3. TIACUMICIN A $^1$H NMR SPECTRUM IN METHANOL $d_4$

FIGURE 4. TIACUMICIN B ULTRAVIOLET SPECTRUM
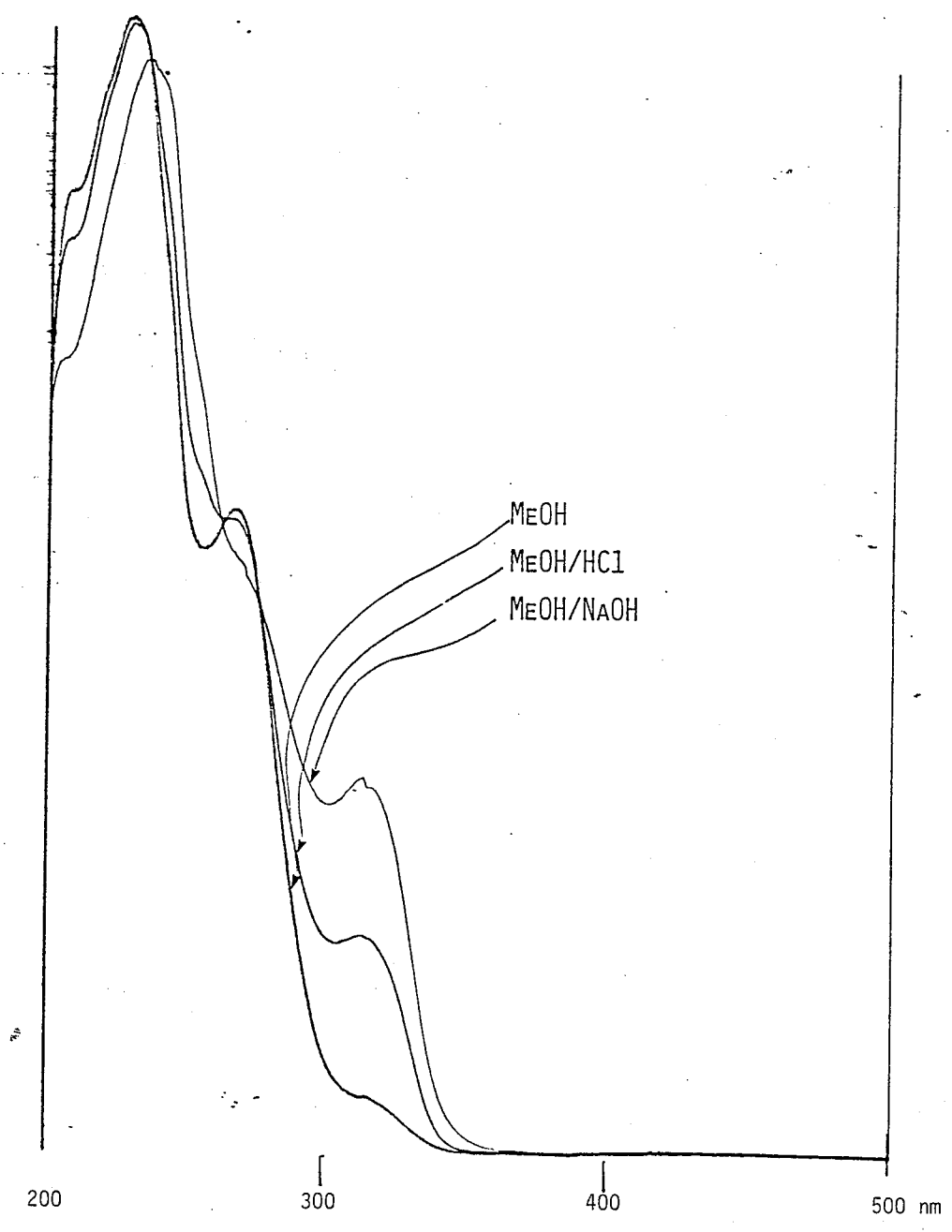

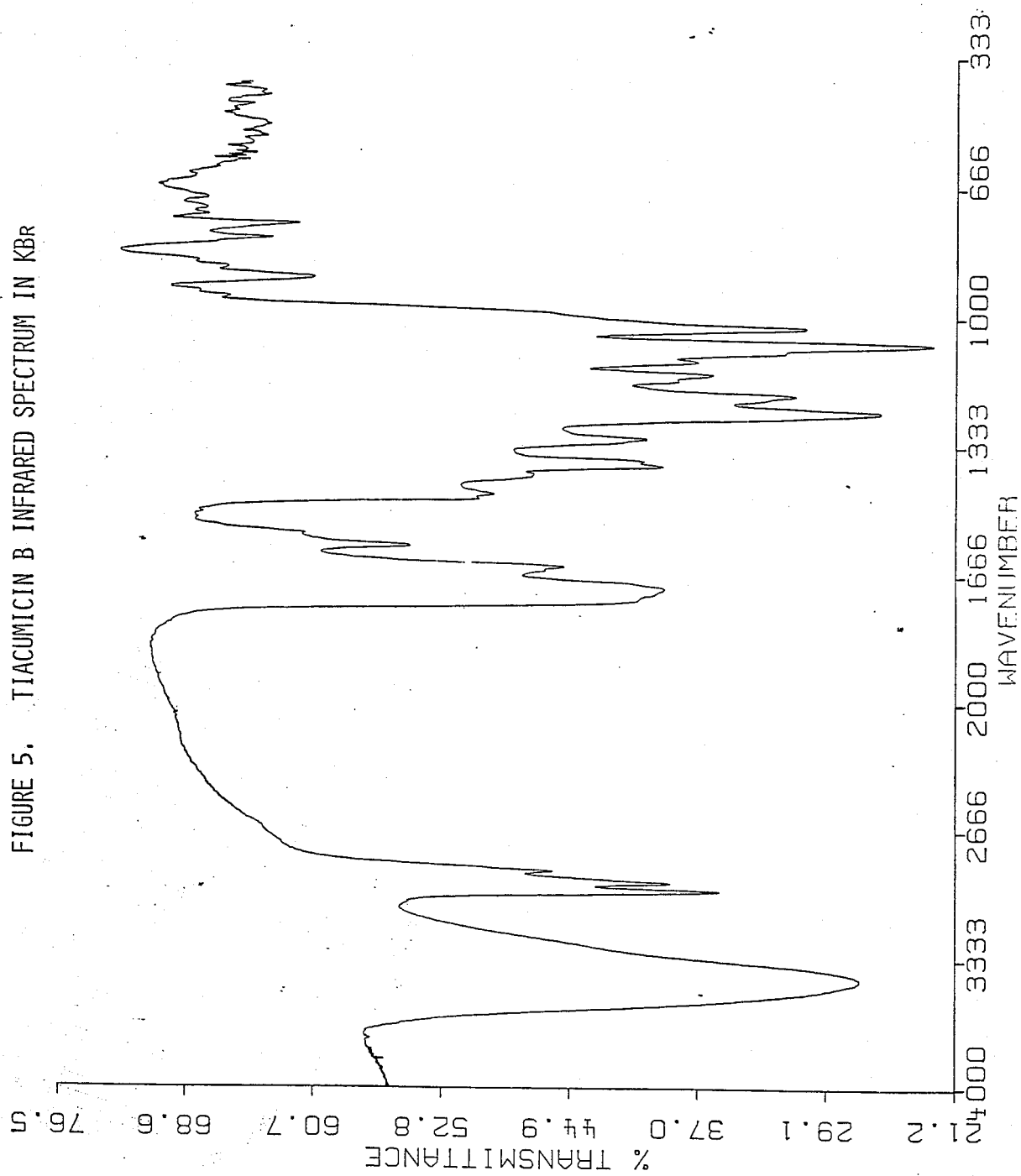

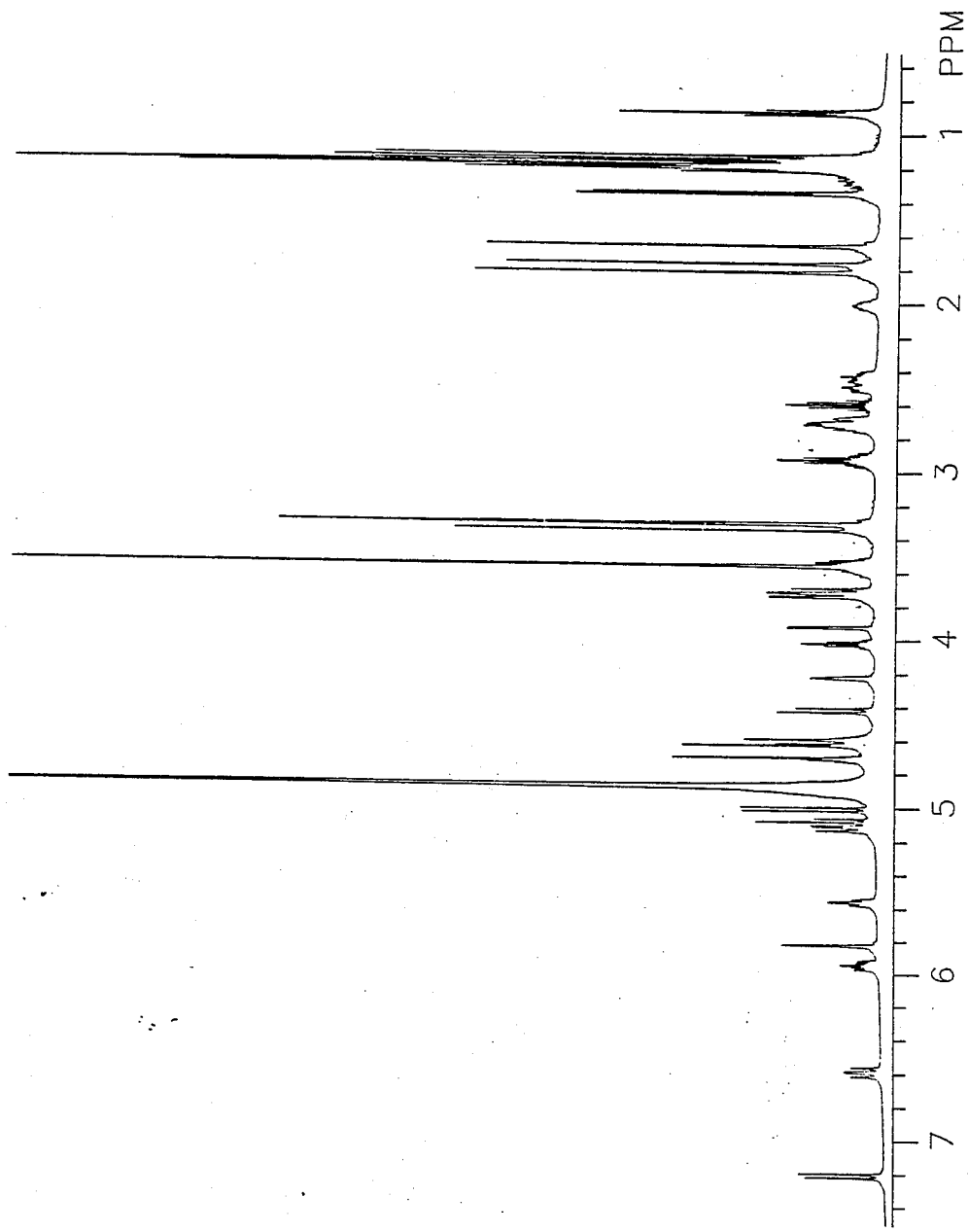
FIGURE 6. TIACUMICIN B $^1$H NMR SPECTRUM IN METHANOL $d_4$

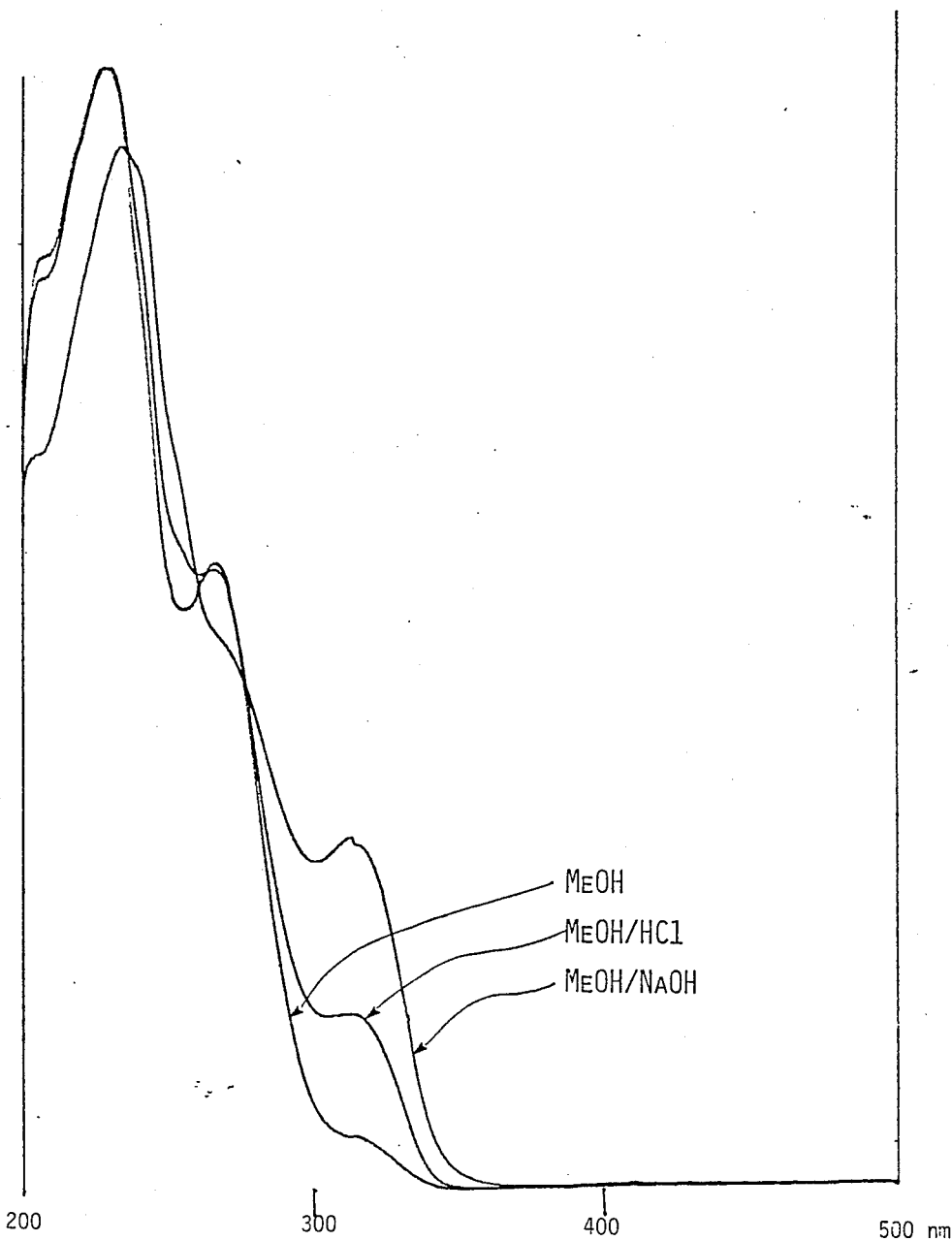
FIGURE 7. TIACUMICIN C ULTRAVIOLET SPECTRUM

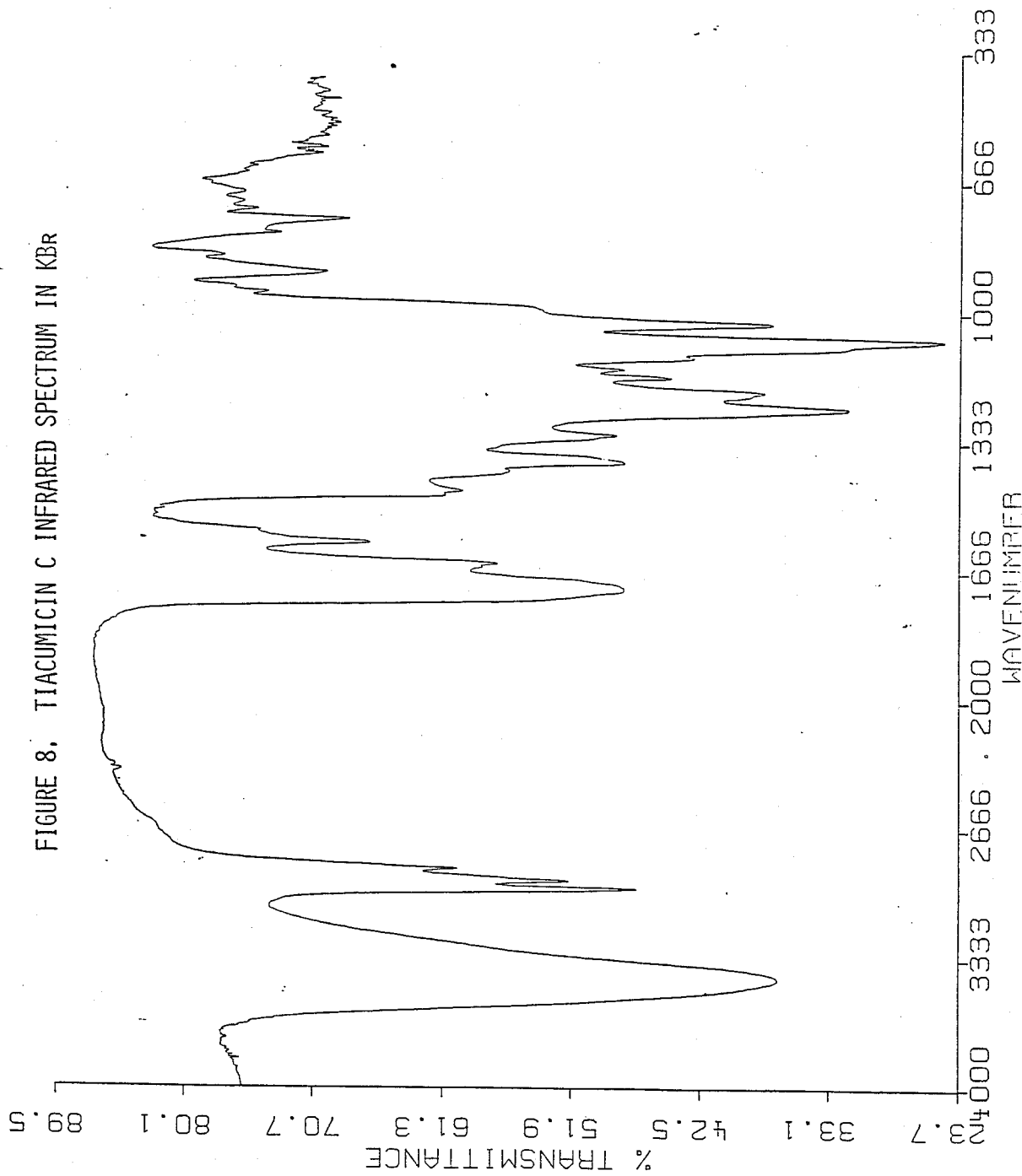
FIGURE 8. TIACUMICIN C INFRARED SPECTRUM IN KBr

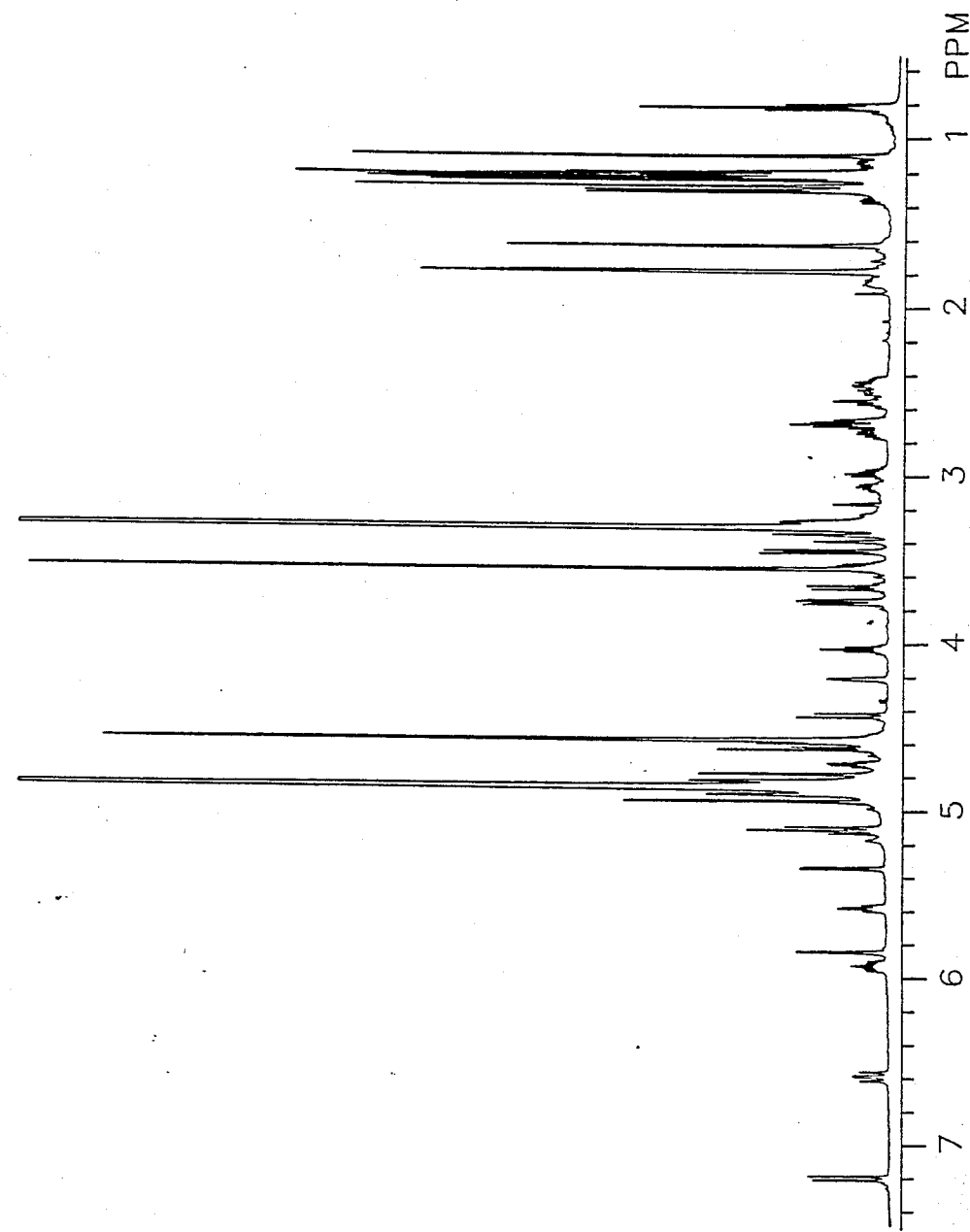
FIGURE 9. TIACUMICIN C $^1$H NMR SPECTRUM IN METHANOL $d_4$

FIGURE 10: TIACUMICIN D ULTRAVIOLET SPECTRUM
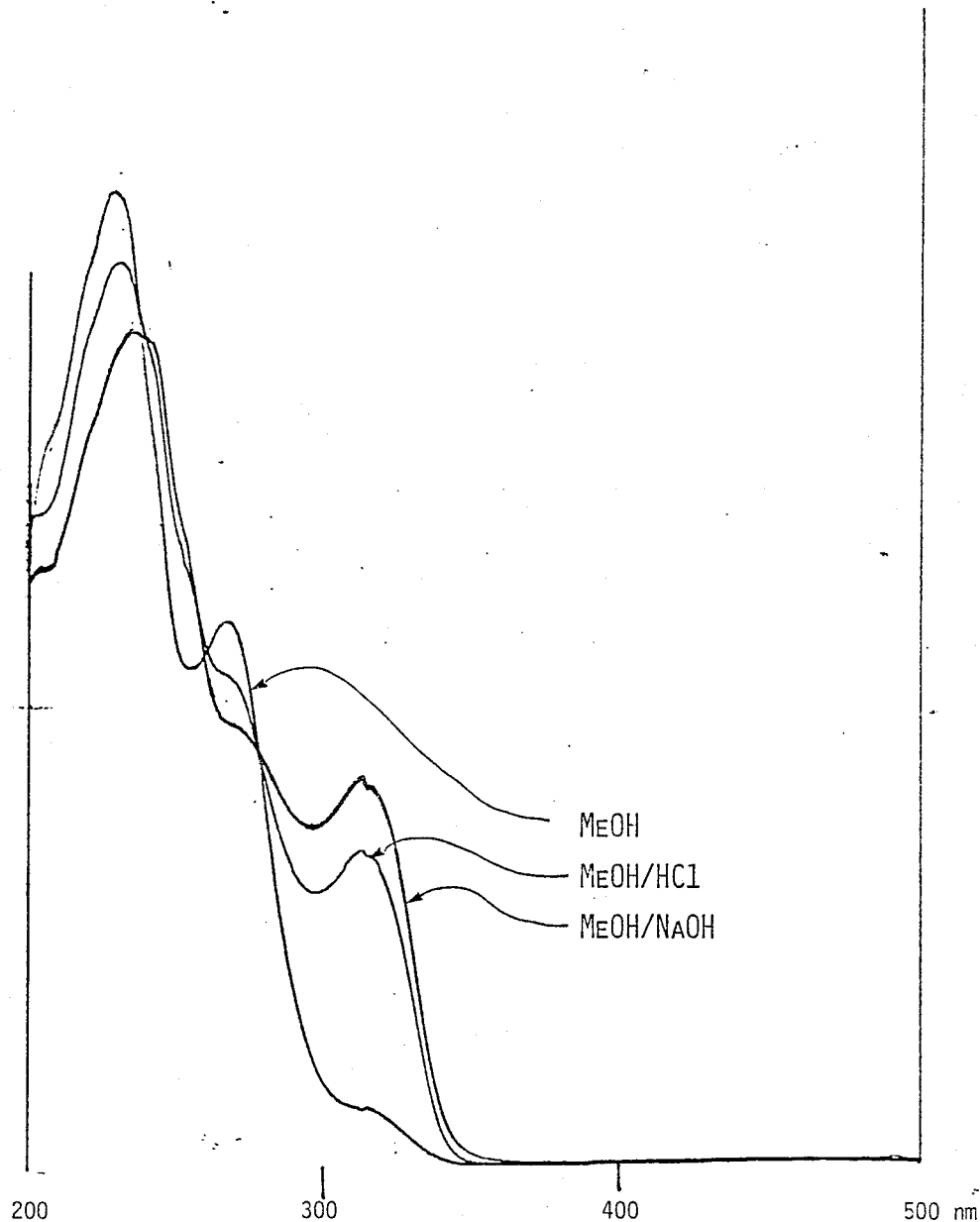

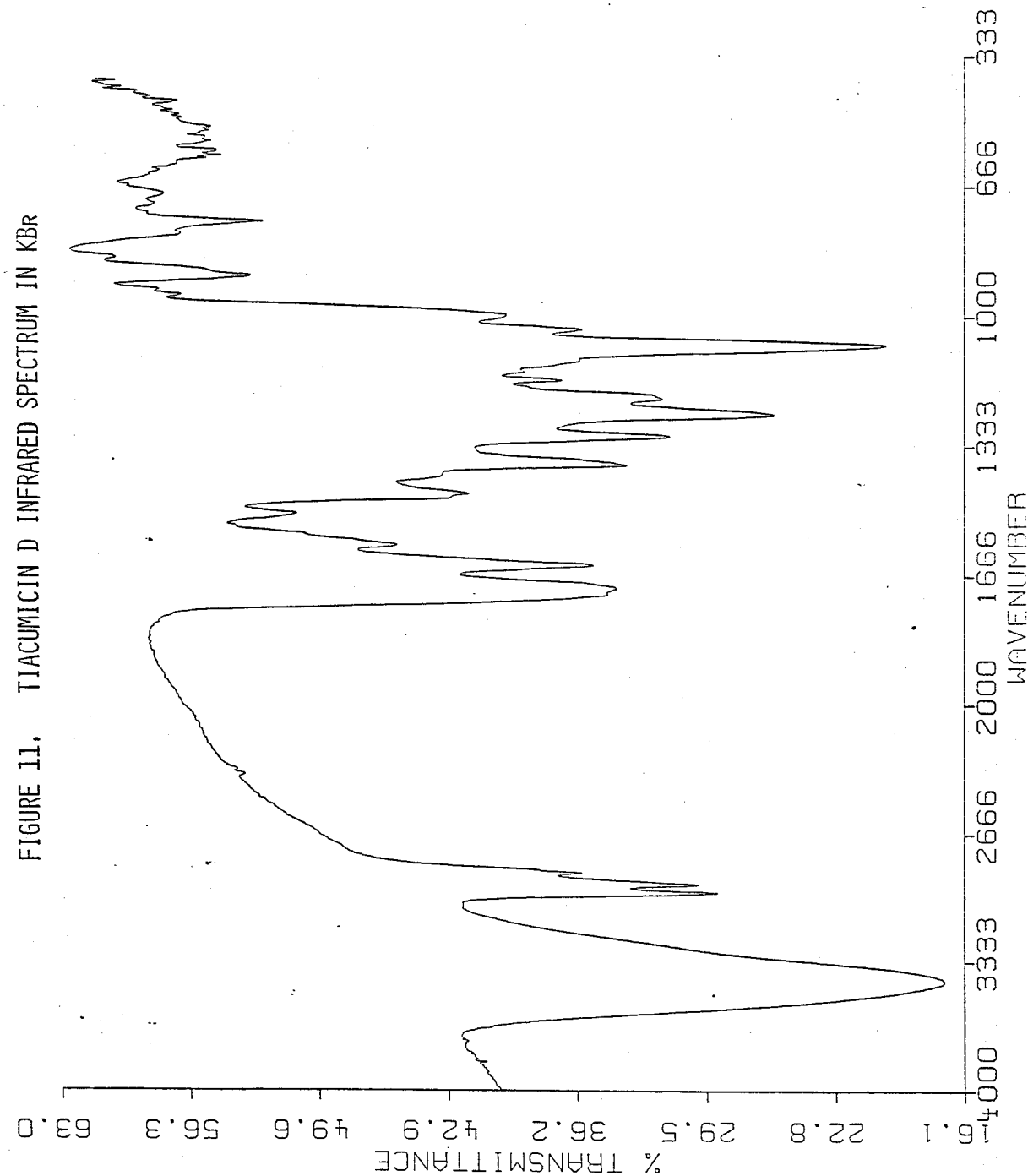
FIGURE 11. TIACUMICIN D INFRARED SPECTRUM IN KBr

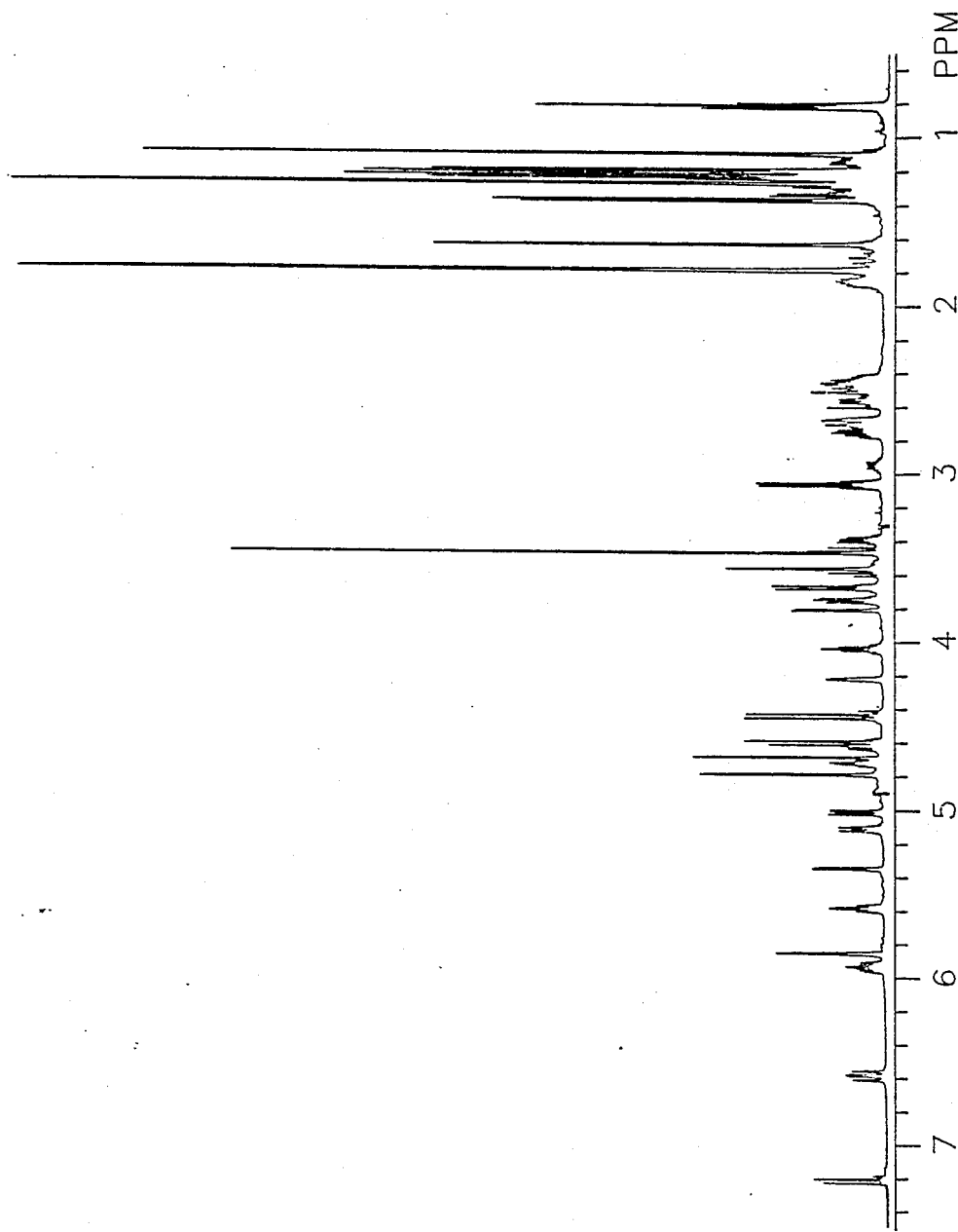
FIGURE 12. TIACUMICIN D $^1$H NMR SPECTRUM IN METHANOL $d_4$

FIGURE 13. TIACUMICIN E ULTRAVIOLET SPECTRUM
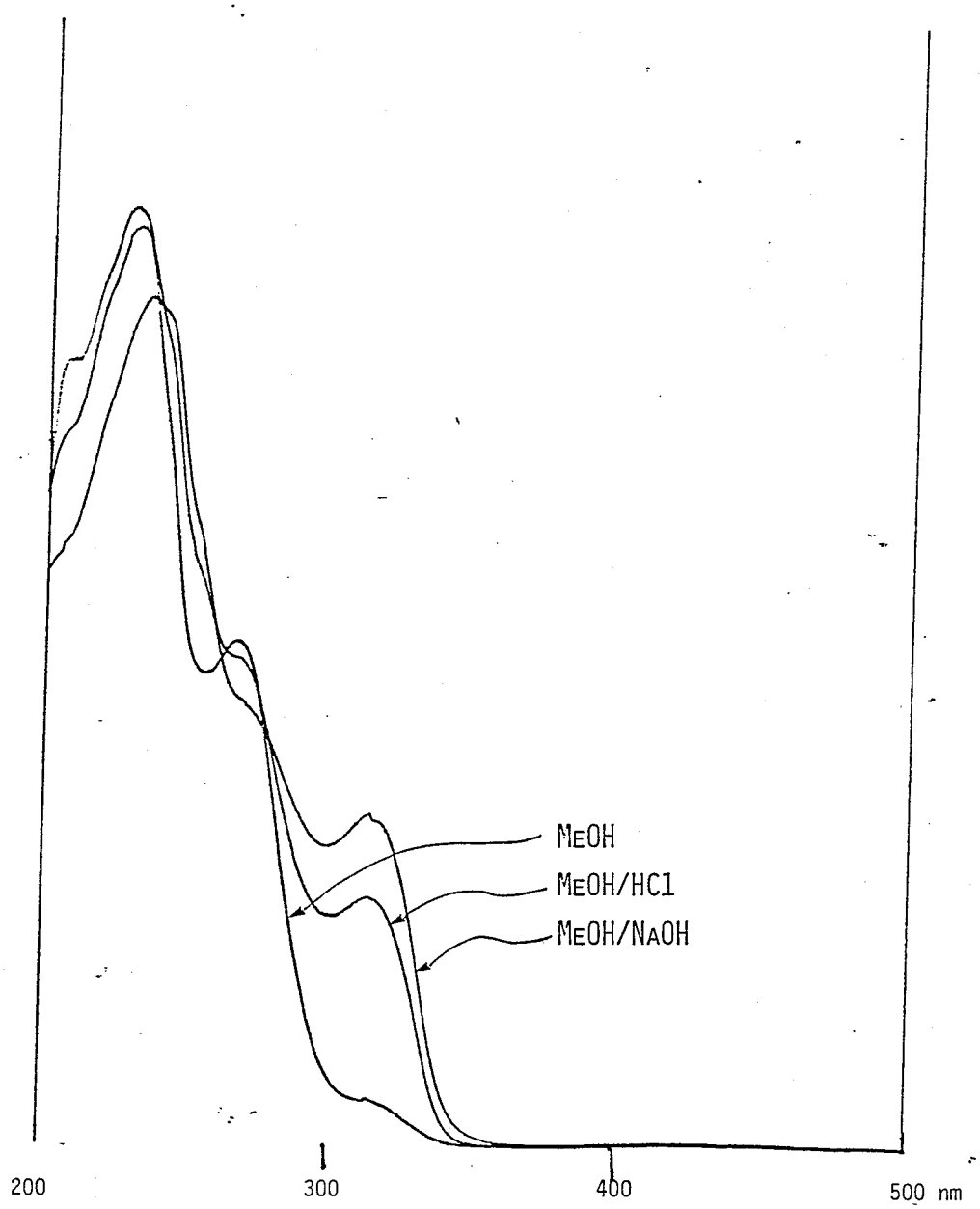

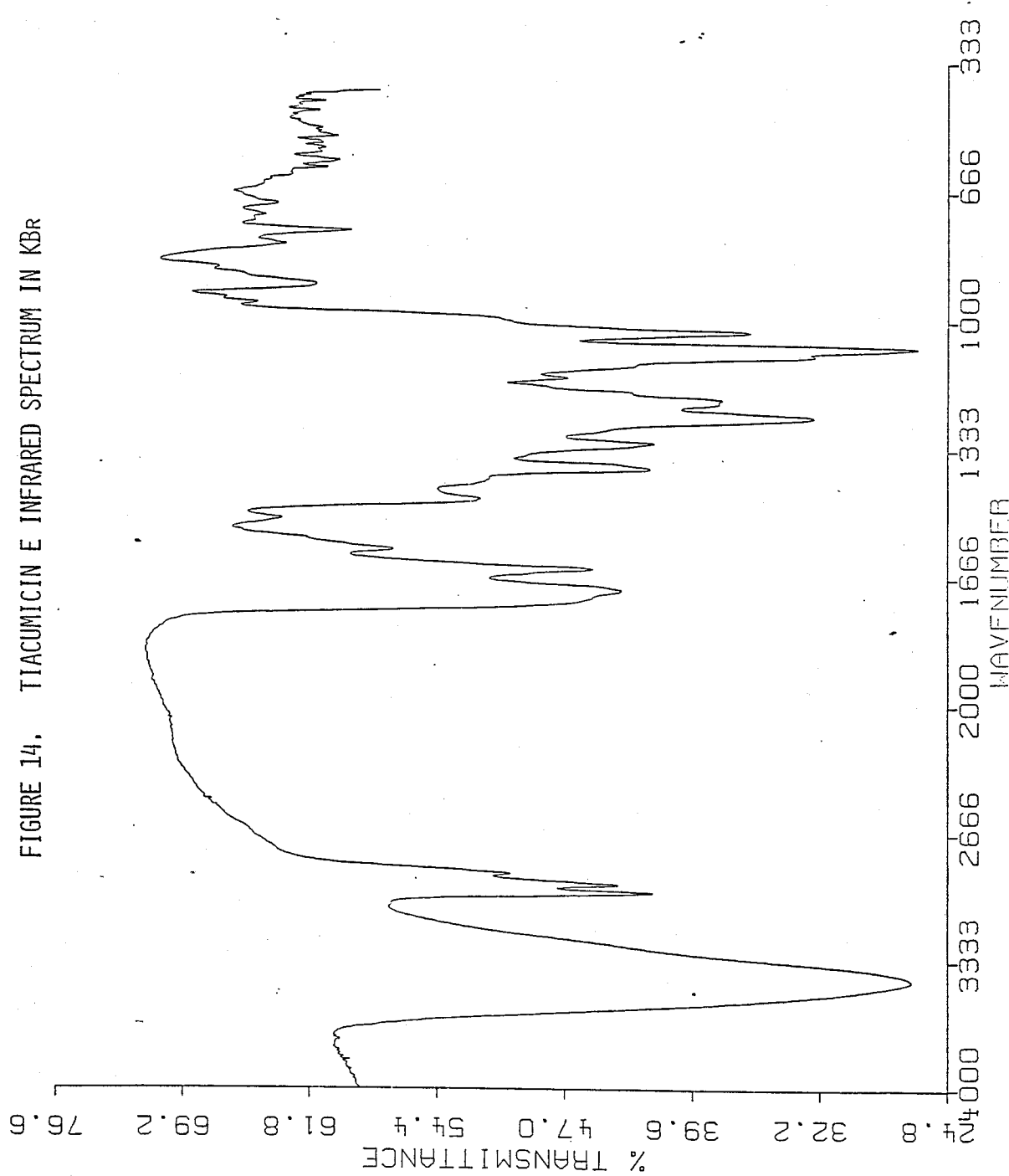
FIGURE 14. TIACUMICIN E INFRARED SPECTRUM IN KBr

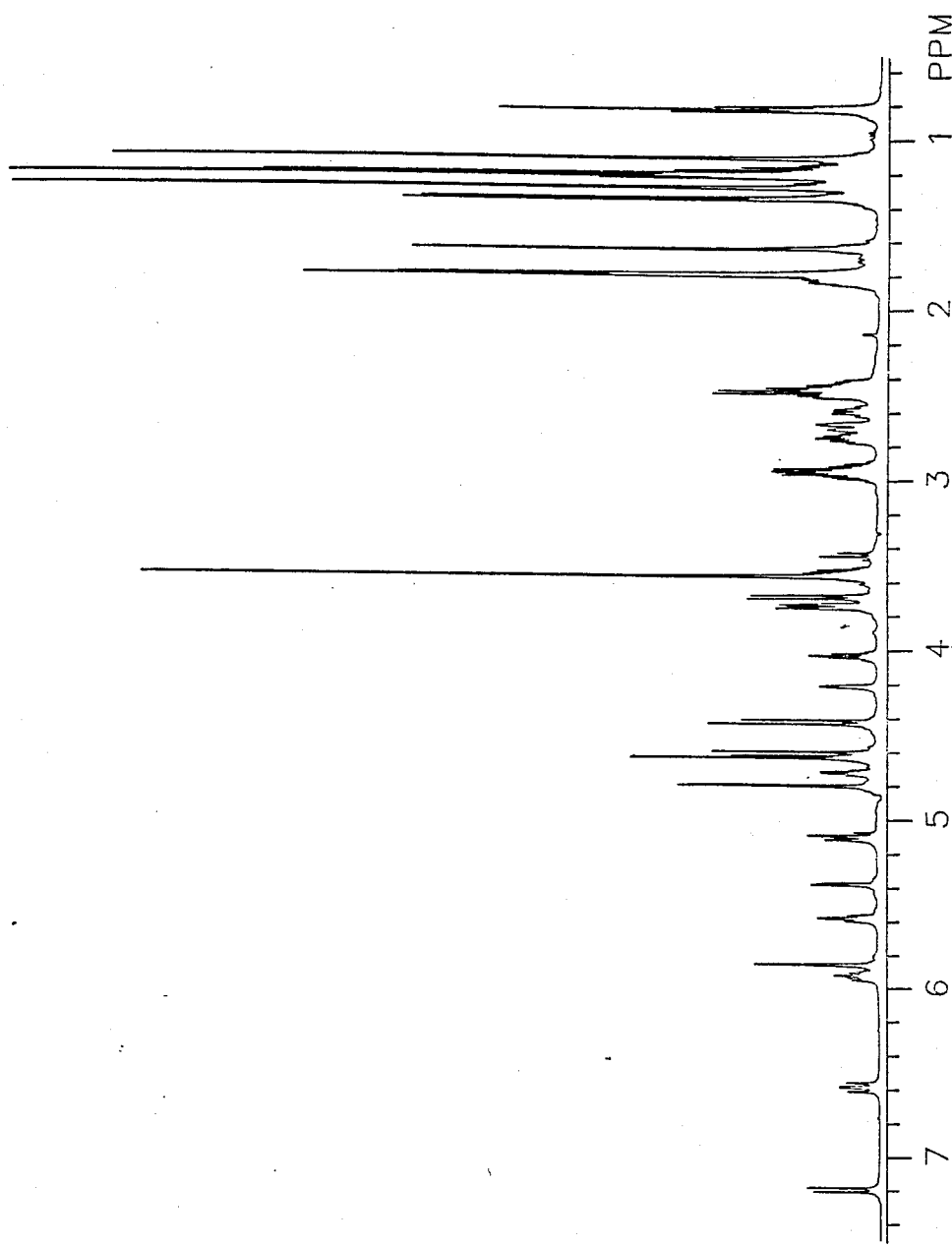
FIGURE 15. TIACUMICIN E $^1$H NMR SPECTRUM IN METHANOL $d_4$

FIGURE 16. TIACUMICIN F ULTRAVIOLET SPECTRUM
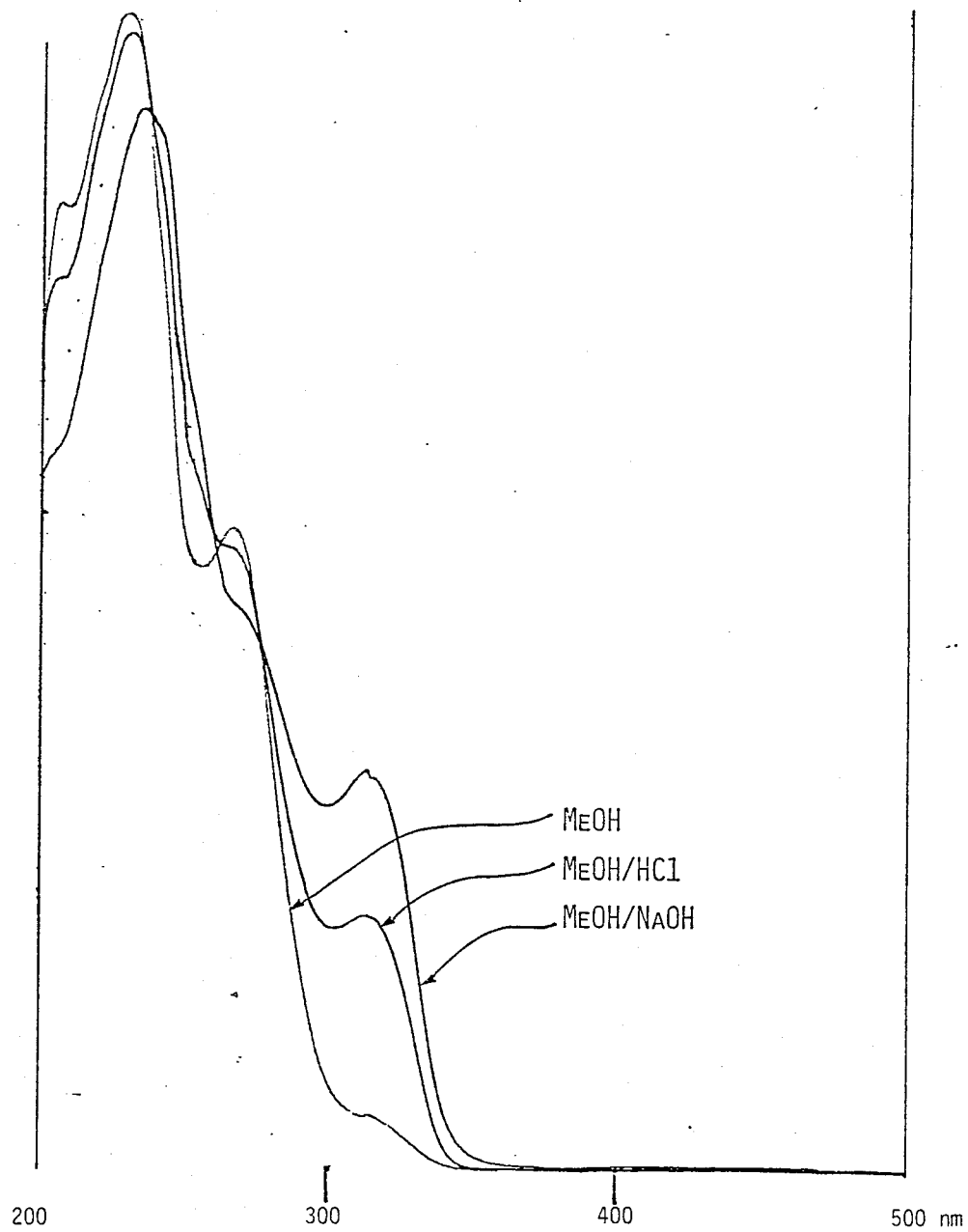

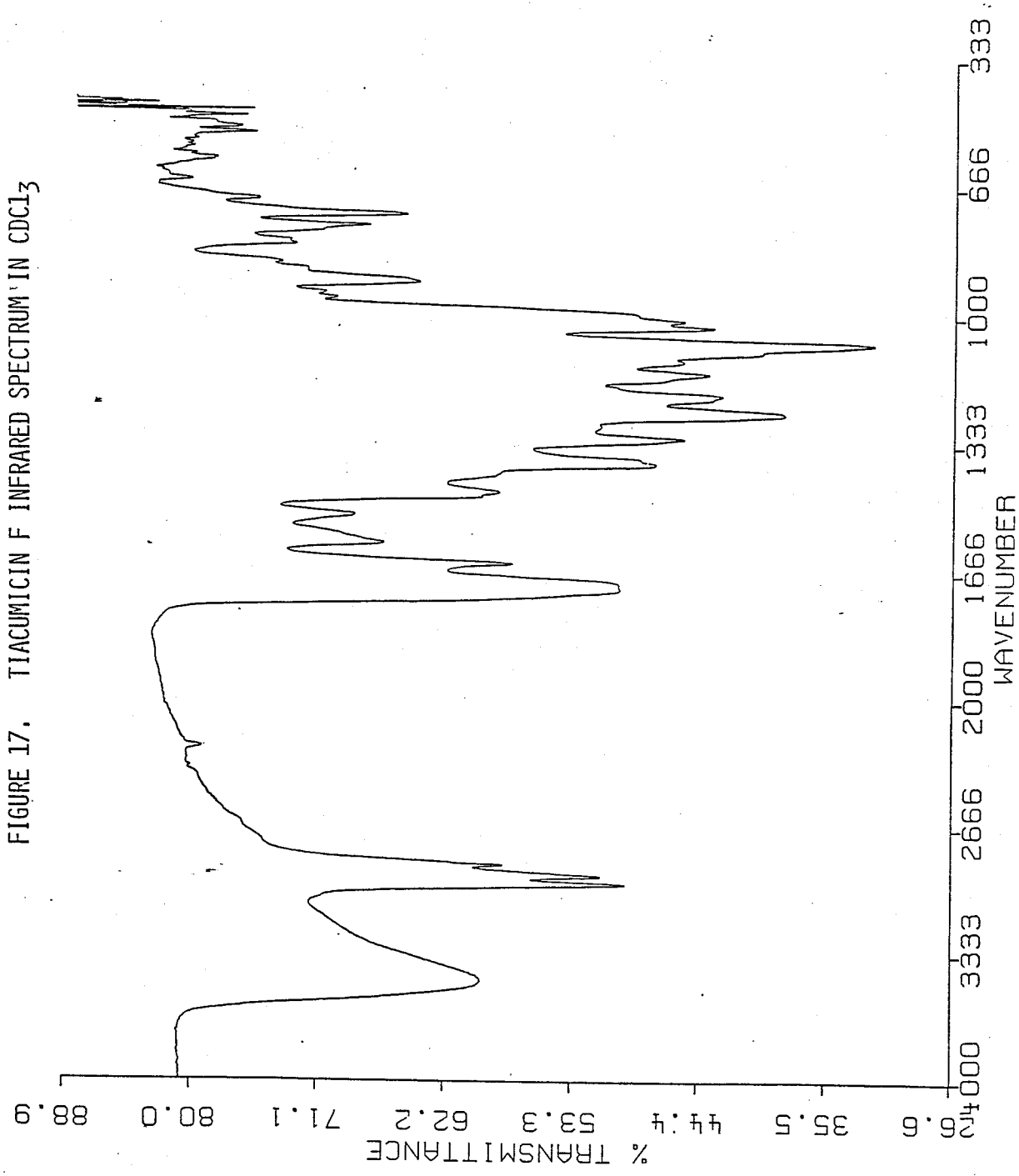
FIGURE 17. TIACUMICIN F INFRARED SPECTRUM IN CDCl₃

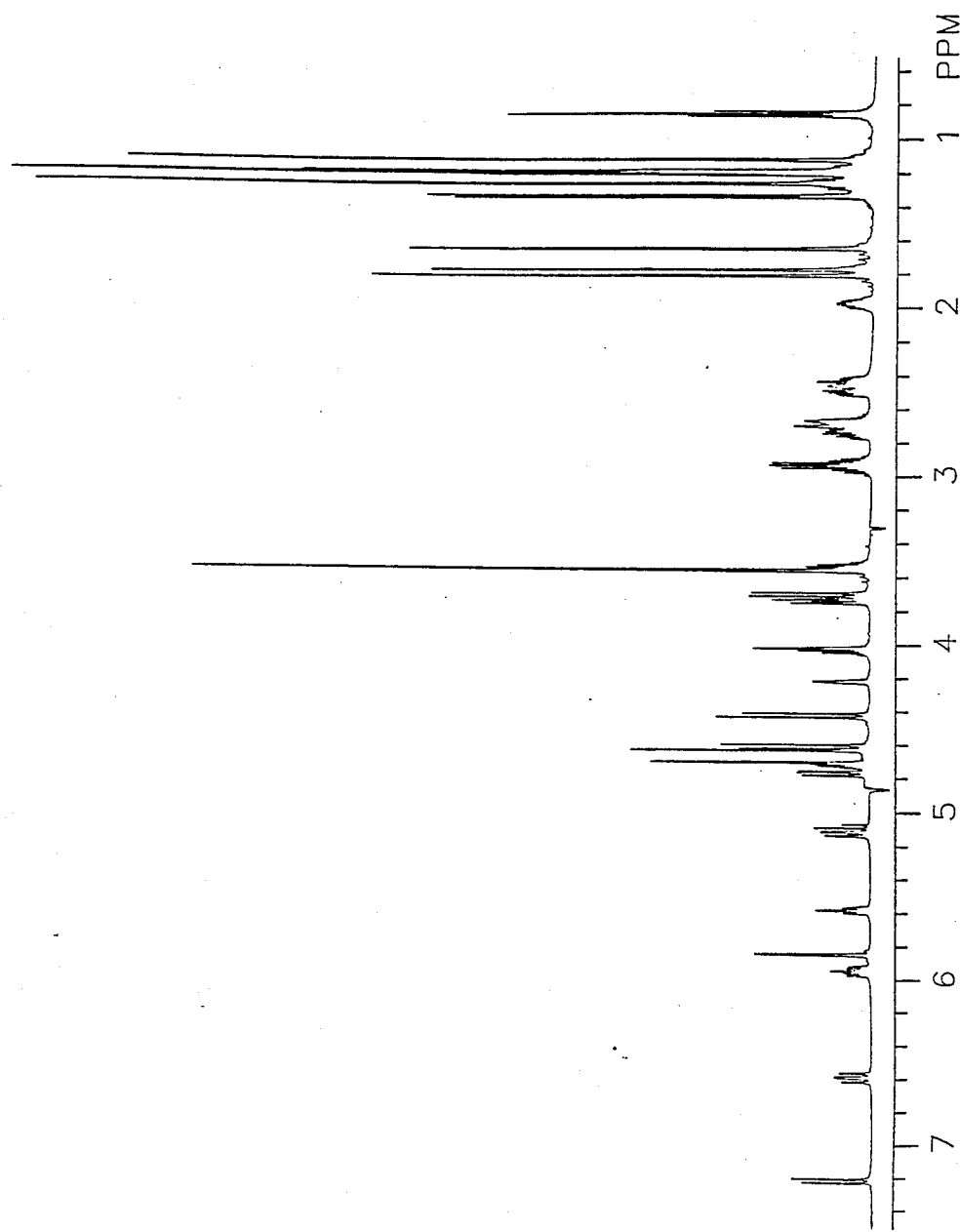
FIGURE 18. TIACUMICIN F ¹H NMR SPECTRUM IN METHANOL d₄

TIACUMICIN COMPOUNDS

TECHNICAL FIELD

This invention relates to new antibiotic agents and a process for making the same.

BACKGROUND ART AND DISCLOSURE OF THE INVENTION

Numerous antibiotics in the prior art, which exhibit activity against a broad spectrum of Gram-positive bacteria, have been produced from species of microorganisms which have been isolated from soil samples throughout the world. Such antibiotics continue to be in demand.

The new compounds of the present invention have been named tiacumicin. They are believed to be of the following chemical structure I

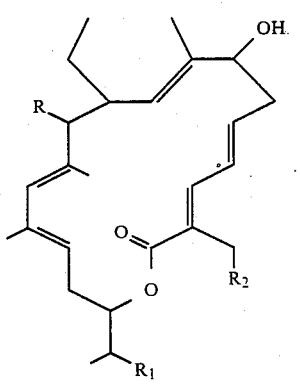

wherein R is a substituent of the formula

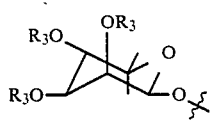

wherein each $R_3$ is a hydrogen or a $C_1$ to $C_4$ fatty acid;
wherein $R_1$ is hydrogen or hydroxy; and wherein $R_2$ is hydrogen or a substituent of the formula

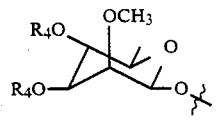

wherein one $R_4$ is hydrogen and the other is a substituent of the formula

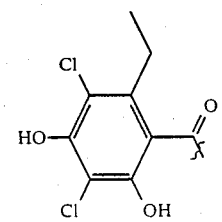

Preferred compounds of the present invention include compounds which have been named tiacumicin A through F. Tiacumicin A is the compound of formula I wherein R is the following substituent

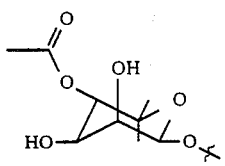

and $R_2$ and $R_3$ are hydrogen.

Tiacumicin B is the compound of formula I where R is the following substituent

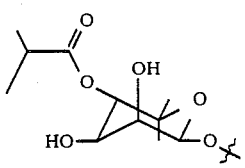

$R_1$ is hydroxy; and $R_2$ is a substituent of the formula

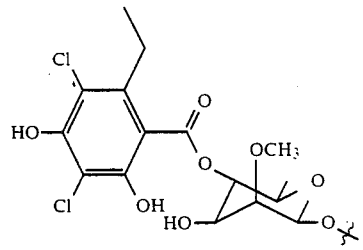

Tiacumicin C is the compound of formula I where R is a substituent of the following formula

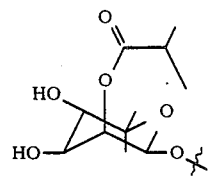

$R_1$ is hydroxy; and $R_2$ is a substituent of the following formula

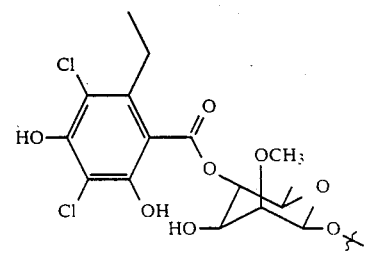

Tiacumicin D is a compound of formula I where R is a substituent of the following formula

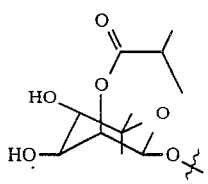

$R_1$ is hydroxy; and $R_2$ is a substituent of the following formula:

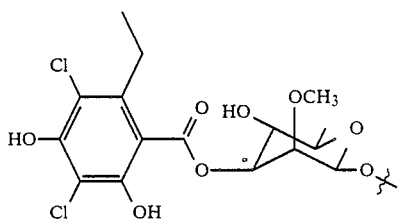

Tiacumicin E is a compound of formula I where R is a substituent of the following formula:

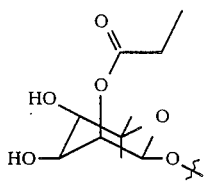

$R_1$ is hydroxy; and $R_2$ is a substituent of the formula:

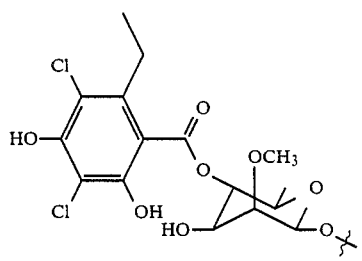

Finally, Tiacumicin F is a compound of formula I wherein R is a substituent of the following formula:

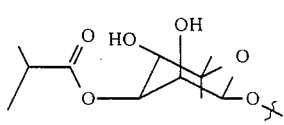

$R_1$ is hydroxy; and $R_2$ is a substituent of the formula:

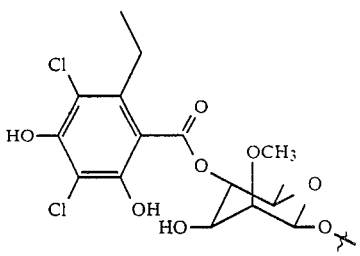

BRIEF DESCRIPTION OF THE DRAWINGS

FIG. 1 illustrates the ultraviolet absorption spectra of tiacumicin A in methylalcohol; a mixture of methylalcohol and hydrochloric acid; and in a mixture of methylalcohol and sodium hydroxide;

FIG. 2 illustrates the infrared spectrum of tiacumicin A in $CDCl_3$;

FIG. 3 illustrates the hydrogen nuclear magnetic resonance spectrum of tiacumicin A in methanol $d_4$;

FIG. 4 illustrates the ultraviolet absorption spectra of tiacumicin B in methylalcohol; in a mixture of methylalcohol and hydrochloric acid; and in a mixture of methylalcohol and sodium hydroxide;

FIG. 5 illustrates the infrared absorption spectrum of tiacumicin B in a potassium bromide pellet;

FIG. 6 illustrates the hydrogen nuclear magnetic resonance spectrum of tiacumicin B in methanol $d_4$;

FIG. 7 illustrates the ultraviolet absorption spectra of tiacumicin C in methylalcohol; in a mixture of methylalcohol and hydrochloric acid; and in a mixture of methylalcohol and sodium hydroxide;

FIG. 8 illustrates the infrared absorption spectrum of tiacumicin C in a potassium bromide pellet;

FIG. 9 illustrates the hydrogen nuclear magnetic resonance spectrum of tiacumicin C in methanol $d_4$;

FIG. 10 illustrates the ultraviolet absorption spectra of tiacumicin D in methylalcohol; in a mixture of methylalcohol and hydrochloric acid; and in a mixture of methylalcohol and sodium hydroxide;

FIG. 11 illustrates the infrared absorption spectrum of tiacumicin D in a potassium bromide pellet;

FIG. 12 illustrates the hydrogen nuclear magnetic resonance spectrum of tiacumicin D in methanol $d_4$;

FIG. 13 illustrates the ultraviolet absorption spectra of tiacumicin E in methylalcohol; in a mixture of methylalcohol and hydrochloric acid; and in a mixture of methylalcohol and sodium hydroxide;

FIG. 14 illustrates the infrared absorption spectrum of tiacumicin in a potassium bromide pellet;

FIG. 15 illustrates the hydrogen nuclear magnetic resonance of tiacumicin E in methanol $d_4$;

FIG. 16 illustrates the ultraviolet absorption spectra of tiacumicin F in methylalcohol; in a mixture of methyl alcohol and hydrochloric acid; and in a mixture of methyalcohol and sodium hydroxide;

FIG. 17 illustrates the infrared absorption spectrum of tiacumicin F in $CDCl_3$; and FIG. 18 illustrates the hydrogen nuclear magnetic resonance spectrum of tiacumicin F in methanol $d_4$.

BEST MODE FOR CARRYING OUT THE INVENTION

This invention encompasses the novel antibiotic agents Tiacumicin A through F produced by submerged aerobic fermentation of the microorganism *Dactylosporangium aurantiacum* subspecies *hamdenensis*. The compounds described exhibit antibiotic acivity against a number of Gram positive bacteria including *Staphylococcus aureus, S. epidermidis, Micrococcus luteus, Streptococcus faecium, S. pyrogenes,* and *Propionibacterium acnes.* The antibiotics were recovered from the fermentation broth by ethyl acetate extraction and from the mycelium by acetone steep. Purification involved solvent-solvent partitioning, sephadex LH-20 ®, coil planet centrifuge, and silica gel chromatographies.

I. The Microorganism

The microorganism employed in this invention was isolated from a soil sample collected in Hamden, Conn. The culture was identified as belonging to the family Actinoplanaceae, genus Dactylosporangium. It has been designated *Dactylosporangium aurantiacum* subspecies *hamdenensis* 718C-41. A representative culture of this microorganism was deposited with the ARS Patent Collection of the Northern Regional Research Center, United States Department of Agriculture, 1815 North University Street, Peoria, Ill., 61604, U.S.A. where it was assigned accession number NRRL 18085. Subcultures of the microorganism are available on request from this agency.

The characteristics of strain AB 718C-41 are given in the following paragraphs.

II. Morphology

The microorganism shows moderate growth on a variety of culture media. The extensive substrate mycelium is usually colored moderate orange to orange yellow. No aerial mycelium is formed. Masses of finger-shaped sporangia are formed on the surface of some agar media. The sporangia, which typically measure 0.8×2.5–3.5 μm, contain a single row of two to four spores. The spores become motile about 45 minutes after being suspended in water. Globose bodies were observed on some media.

III. Chemotaxonomy

Analysis of whole-cell hydrolysates of strain AB 718C-41 by the method of Lechevalier (J. Lab. Clin. Med. 71: 934–944, 1968) revealed the presence of hydroxydiaminopimelic acid. Xylose, arabinose and galactose were the diagnostic sugars detected in the whole-cell hydrolysates.

IV. Cultural and Physiological Characteristics

Most of the cultural and physiological characteristics and the carbon utilization pattern of *Dactylosporangium aurantiacum* subsp. *hamdenensis* were determined using the methods and media suggested by Shirling and Gottlieb (Intern. J. Syst. Bacteriol. 16: 313–340, 1966) and Waksman (*The Actinomycetes*, Vol. II pp. 328–334, The Williams and Wilkins Co., 1961 and Bacteriol. Rev. 21: 1–29, 1957). Starch, tyrosine and casein hydrolyses, however, were performed using the method of Gordon et al. (Intern. J. Syst. Bateriol. 24, 54–63, 1971). The culture characteristics of strain AB 718C-41 are given in Table I, and Table II shows the carbon utilization pattern. The physiological characteristics of the strain are reported in Table III. All observations were made after incubation at 28° C. for 14 days.

TABLE I

| | Cultural Characteristics | | |
|---|---|---|---|
| Culture Medium | Color of Vegatative Mycelium | Growth | Soluble Pigment |
| ISP No. 2 (yeast extract - malt extract agar) | Moderate orange (53)* | Abundant | Absent |
| ISP No. 3 (oatmeal agar) | Pale orange yellow (73) with strong orange (50) spots | Moderate | Absent |
| ISP No. 4 (inorganic salts-starch agar) | Light orange yellow (70) | Moderate | Absent |
| ISP No. 5 (glycerol-asparagine agar) | Light orange yellow (70) | Moderate | Absent |
| ISP No. 6 (peptone-yeast extract-iron agar) | Moderate orange yellow (71) | Moderate | Absent |
| ISP No. 7 (tyrosine agar) | Light orange (52) | Moderate | Absent |
| Czapek sucrose agar | Pale orange yellow (73) with strong orange (50) spots | Poor | Absent |
| Nutrient agar | Light orange yellow (70) | Moderate | Absent |
| Calcium maltate agar | Yellow white (92) | Moderate | Absent |
| ATCC No. 172 | Light orange (52) with strong brown (55) spots | Abundant | Absent |

TABLE II

| Utilization of Carbon Sources | |
|---|---|
| Compound | Growth |
| Glucose | ++ |
| L—Arabinose | ++ |
| D-Xylose | ++ |
| Inositol | − |
| D-Fructose | ++ |
| Sucrose | + |
| Rhamnose | ++ |
| Raffinose | ++ |
| Mannitol | ++ |
| D-Galactose | ++ |
| Salicin | + |
| Cellulose | − |
| None | − |

+ Growth
++ Good growth
− No growth

TABLE III

| Physiological Characteristics | |
|---|---|
| Test | Reaction |
| H$_2$S Production | + |
| Gelatin Liquefaction | − |
| Casein Hydrolysis | + |
| Starch Hydrolysis | + |
| Tyrosine Hydrolysis | + |
| Nitrate Reduction | + |
| Milk Peptonization | + |
| Milk Coagulation | − |
| Calcium Maltate Hydrolysis | − |
| Melanin Formation* | − |
| Growth Temperature Range** | 15–37° C. |
| NaCl Tolerance*** | 1.5% |

*Peptone - yeast extract - iron agar (ISP 6) Tyrosine Agar (ISP 7)
**Hickey - Tresner Agar
***Nutrient Agar The occurrence of globose bodies and typical finger-shaped sporangia containing motile spores, the presence of hydroxydiaminopimelic acid and arabinose and xylose in whole-cell hydrolysates, and the overall colony morphology and pigmentation indicate that the microorganism described in this invention is a member of the genus Dactylosporangium Strain AB 718C-41 differs in only minor characteristics (temperature growth range, mycelial pigment intensity) from the Dactylosporangium type species, *D. aurantiacum*, which was described by Thiemann et. al. (Arch. fur Mikrobiol 58: 42–52, 1967). Hence, we have designated it a new subspecies of this species, *D. aurantiacum* subsp. *hamdenensis*.

V. Fermentation

Cultivation of *Dactylosporangium aurantiacum* subsp. *hamdenensis* AB 718C-41 NRRl 18085 for the production of the tiacumicins is carried out in liquid media. Assimilable carbon sources such as glucose and soybean oil are combined with an organic nitrogen source such as soybean flour, beef extract or peptone and inorganic salts. $GaCO_3$ is added to aid in controlling the pH of the fermentation. Other organic and inorganic ingredients may be added to stimulate production of the antibiotic.

A liquid submerged, stirred culture process is preferred for the production of the antibiotic. Fermentations are carried out at a temperature range of 25° to 35° C. The pH of the fermentation is preferably maintained between 6 and 9. The antibiotic is produced and accumulated between 3 and 9 days after inoculation of the fermentation.

VI. Antibiotic Recovery

Upon completion of fermentation the whole broth was adjusted to pH 7 and the mycelial mass removed. The filtered broth was extracted three times with ethyl acetate, the extracts combined and concentrated to an oily residue. This residue was further purified by trituration with low polarity solvents such as hexane and heptane, or by partitioning between two phase solvent systems such as hexane/methanol or chloroform/carbon tetrachloride/ethyl acetate/methanol/water mixtures in various ratios and combinations, or by Sephadex LH-20 ® column chromatography eluted with an appropriate organic solvent system. Antibiotic components were separated by either silica gel or coil planet centrifuge chromatography or both.

VII. Characterization of Tiacumicins A–F

Tiacumicin A $[\alpha]_D^{25} = +41$ (c=0.1, MeOH) was a clear oil with $R_f$=0.75 in $CHCl_3$/MeOH 9:1, 0.85 in EtOAc/MeOH 4:1, and 0.05 in acetone/benzene 1:4 on an Analtech silica gel TLC plate. Tiacumicin A was readily soluble in chloroform, methanol and benzene, sparingly soluble in acetone and acetonitrile and insoluble in water. A molecular weight of 604 was established by FAB negative ion mass spectroscopy. An ultraviolet spectrum in MeOH, contained bands at $\lambda_{max}$=203 nm ($\epsilon$=6785), 235 (6410), 266 (4960) (see FIG. 1). These bands were unchanged upon addition of acid or base. An infrared spectrum measured neat contained bands at: 3480, 2930, 1735, 1700, 1460, 1370, 1240, 1150, 1115, 1080, 1040 $CM^{-1}$. A $^1H$ NMR spectrum run in $d_4$ MeOH at 360 MHz is supplied (see FIG. 3).

Tiacumicin B $[\alpha]_D^{25} = -6.5°$ (c=8.2, MeOH) m.p.=143°–145° C. had an $R_f$ of 0.62 in $CHCl_3$/MeOH 9:1, 0.81 in EtOAc/MeOH 4:1, and 0.02 in acetone/benzene 1:4 on an Analtech silica gel TLC plate. Tiacumicin B was readily soluble in methanol and acetonitrile, sparingly soluble in chloroform, benzene and ether, and insoluble in hexane and water. A molecular weight of 1056 was established by FAB positive and negative ion mass spectrometry. An ultraviolet spectrum in MeOH contained bands at $\lambda_{max}$=206 nm ($\epsilon$=13,940), 229 (17,430), 266 (9,300), 314 (2965), in MeOH/HCl at $\lambda_{max}$=206 nm ($\epsilon$=142,815), 229 (17,778), 266 (9360), 314 (870) and in MeOH/NaOH at $\lambda_{max}$=204 nm ($\epsilon$=32,500), 232 (17,110), 235 (shoulder), 255 (shoulder), 270 (shoulder), 314 (8220) (see FIG. 4). An infrared spectrum measured in KBr contained bands at: 3565, 3502, 2978, 2935, 2880, 1735, 1695, 1665, 1590, 1465, 1455, 1410, 1402, 1380, 1370, 1320, 1310, 1240, 1215, 1195, 1140, 1065, 1020 $cm^{-1}$ (see FIG. 5). A $^1H$ NMR spectrum run in $d_4$ MeOH at 500 MHz is supplied (see FIG. 6).

Tiacumicin C, $[\alpha]_D^{25} = -8.6°$ (c=15.8, MeOH), m.p.=142°–143° C. had an $R_f$ of 0.37 in $CHCl_3$/MeOH 9:1, 0.80 in EtOAc/MeOH 4:1, and 0.0 in acetone/benzene 1:4 on an Analtech silica gel TLC plate. Tiacumicin C was readily soluble in methanol and acetonitrile, sparingly soluble in chloroform, benzene and ether, and insoluble in hexane and water. A molecular weight of 1056 was established by FAB positive ion mass spectrometry. An ultraviolet spectrum in MeOH contained bands at $\lambda_{max}$=206 nm ($\epsilon$=25,096), 228 (29,630), 267 (15,410), 315 (630), in MeOH/HCl at $\lambda_{max}$=206 nm ($\epsilon$=25,740), 228 (29,630), 267 (15,555), 315 (1222), and in MeOH/NaOH at $\lambda_{max}$=203 nm ($\epsilon$=29,815), 234 (26,500), 240 (shoulder), 255 (shoulder), 276 (shoulder), 315 (11,555) (see FIG. 7). An infrared spectrum measured in KBr contained bands at: 3565, 2990, 2945, 2880, 1735, 1695, 1650, 1595, 1470, 1455, 1415, 1405, 1390, 1370, 1310, 1250, 1230, 1200, 1165, 1145, 1115, 1090, 1070, 1025 $cm^{-1}$ (see FIG. 8). A $^1H$ NMR spectrum run in $d_4$ MeOH at 500 MHz is supplied (see FIG. 9).

Tiacumicin D, $[\alpha]_D^{25} = -5.6°$ (c=0.47, MeOH), m.p.=141°–145° C. had an $R_f$ of 0.52 in $CHCl_3$/MeOH 9:1, 0.75 in EtOAc/MeOH 4:1, and 0.04 in acetone/benzene 4:1 on an Analtech silica gel TLC plate. Tiacumicin D was readily soluble in methanol and acetonitrile, sparingly soluble in chloroform, benzene and ether, and insoluble in hexane and water. A molecular weight of 1056 was established by FAB positive ion mass spectrometry. An ultraviolet spectrum in MeOH contained bands at $\lambda_{max}$=205 nm (shoulder) 229 ($\epsilon$=15,957) 266 (8,342), 314 (4,464), in MeOH/HCl at $\lambda_{max}$=205 nm (shoulder), 229 ($\epsilon$=17,200) 266 (9,440), 314 (1,050), and in MeOH/NaOH at $\lambda_{max}$=203 nm (shoulder), 233 ($\epsilon$=13,878), 242 (shoulder), 269 (shoulder), 314 (5,456) (see FIG. 10). An infrared spectrum measured in KBr contained bands at: 3436, 2974, 2933, 2874, 1716, 1700, 1640, 1590, 1508, 1456, 1383, 1308, 1251, 1210, 1071 $cm^{-1}$ (see FIG. 11). A $^1H$ NMR spectrum run in $d_4$ MeOH at 500 MHz is supplied (see FIG. 12).

Tiacumicin E, $[\alpha]_D^{25} = 3.2°$ (c=1.3, MEOH), m.p.=138°–141° C. had an $R_f$ of 0.44 in $CHCl_3$/MeOH 9:1, 0.74 in EtOAc/MeOH 4:1, and 0.03 in acetone/benzene 1:4 on an Analtech silica gel TLC plate. Tiacumicin E was readily soluble in methanol and acetonitrile, sparingly soluble in chloroform, benzene and ether and insoluble in hexane and water. A molecular weight of 1042 was established by FAB positive ion mass spectrometry. An ultraviolet spectrum in MeOH contained bands at $\lambda_{max}$=205 nm (shoulder), 228 ($\epsilon$=49,444), 266 (24,853), 315 (10,170), in MeOH/HCl at $\lambda_{max}$=205 nm ($\epsilon$=40,700), 228 (48,470), 266 (25,730), 315 (1795), and in MeOH/NaOH at $\lambda_{max}$=206 nm (shoulder) 234 ($\epsilon$=43,680), 240 (shoulder), 255 (shoulder), 270 (shoulder), 315 (16,750) (see FIG. 13). An infrared spectrum measured in KBr contained bands at: 3444, 2976, 2935, 2876, 1712, 1700, 1640, 1590, 1456, 1380, 1314, 1247, 1209, 1200, 1087, 1068, 1026 cm$^{-1}$ (see FIG. 14). A $^1$H NMR spectrum run in d$_4$ MeOH at 500 MHz is supplied (see FIG. 15).

Tiacumicin F, $[\alpha]_D^{25} = +5.8$ (c=0.66 MeOH) m.p.=141°–143° C. had an R$_f$ of 0.48 in CHCl$_3$/MeOH 9:1, 0.75 in EtOAc/MeOH 4:1, and 0.03 in acetone/benzene 1:4 on an Analtech silica gel TLC plate. Tiacimicin F was readily soluble in methanol and acetonitrile, sparingly soluble in chloroform, benzene and ether, and insoluble in hexane and water. A molecular weight of 1056 was established by FAB positive ion mass spectrometry. An ultraviolet spectrum in MeOH contained bands at $\lambda_{max}$=204 nm ($\epsilon$=16,245), 228 (20,675) 266 (10,127), 315 (4,747) in MeOH/HCl at $\lambda_{max}$=204 ($\epsilon$=17,510), 228 (21,097), 266 (11,392), 315 (1,055), and in MeOH NaOH at $\lambda_{max}$=202 nm (shoulder), 234 ($\epsilon$=19,304), 240 (shoulder), 255 (shoulder), 315 (7,226) (see FIG. 16). An infrared spectrum measured in CDCl$_3$ contained bands at: 3479, 2975, 2934, 2875, 1709, 1696, 1641, 1588, 1515, 1456, 1381, 1314, 1249, 1200, 1144, 1067, 1022, 908 cm$^{-1}$ (see FIG. 17). A $^1$H spectrum run in d$_4$ MeOH at 500 MHz is supplied (see FIG. 18).

VIII. Bioactivity of Tiacumicins

Tiacumicins B and C possessed antibiotic activity against a number of Gram-positive bacteria in vitro including strains resistant to currently used therapeutic antibiotics (See Table IV).

TABLE IV

Minimal Inhibitory Concentrations (µg/ml) Against Common Test Organisms

| Strain | Tiacumicin A | B | C | D | E | F |
|---|---|---|---|---|---|---|
| Staphylococcus aureus ATCC 6538 | 100 | 12.5 | 50 | >25 | 2.5 | 12.5 |
| Staphylococcus epidermidis 3519 | 100 | 12.5 | 25 | >25 | 12.5 | 12.5 |
| Streptococcus pyogenes 930 | 100 | 12.5 | 25 | >25 | 50 | 12.5 |
| Streptococcus faecium ATCC 8043 | | 12.5 | 100 | >25 | 12.5 | 6.2 |
| Esherichia coli Juhl | | >100 | >100 | >25 | >100 | >100 |
| Pseudomonas aeruginosa A-5007 | | >100 | >100 | >25 | >100 | >100 |
| Micrococcus luteus 9341 | .1 | 0.1 | =<0.39 | .2 | | 6.2 |
| Bacteroides fragilis 784 | | >100 | | | | |
| Propionibacterium acnes 132 | | 6.25 | | | | |
| Candida albicans ATCC 10231 | | >100 | >100 | | | |
| Micrococcus luteus 4698 | .39 | | | | | |

IX. Examples

Example 1

*Dactylosporangium aurantiacum* subsp. *hamdenensis* AB 718C-41 NRRL 18085 was maintained on medium ATCC 172 agar slants, the ingredients for which are shown in table V. Medium S-3 seed tubes (table V) were inoculated from agar slant cultures of AB 718C-41 and incubated on a rotary shaker at 30° C. for 96 hr. (Shakers were set at 250 rpm, 3.2 cm stroke in all studies). At that time 5% vegetative inoculum from the first passage seed tubes was transferred aseptically to medium S-3 seed flasks (table V) which were incubated on a rotary shaker at 30° C. for 72 hr. Five percent vegetative inoculum from the second passage seed flask was then transferred aseptically to fermentation flasks containing the following ingredients:

| Fermentation Medium 6B1 | |
|---|---|
| | gm/liter |
| glucose monohydrate | 10 |
| soybean flour | 10 |
| beef extract (made by Inolex Chemical Co. Chicago, IL) | 3 |
| soybean oil | 1 |
| K$_2$HPO$_4$ | 0.5 |
| MgSO$_4$.7H$_2$O | 0.5 |
| KCl | 0.3 |
| CaCO$_3$ | 3 |

Add distilled water to 1.0 liter
Adjust pH to 7.0

Volume/flask: 100 ml/500 ml Erlenmeyer flask closed with rayon plugs
Sterilization: 30 min, 121° C. 15–16 psi Fermentation flasks were incubated on a rotary shaker at 30° C. for 4 to 6 days. Samples of the whole culture fermentation broth were taken and adjusted to pH 7. The fermentation broth was centrifuged at 1000 rpm for 30 min. The supernatant broth was decanted and then tested for antibiotic activity against a number of strains of pathogenic bacteria in an agar diffusion inhibition zone test. The fermentation broth inhibited antibiotic sensitive and resistant strains of *Astaphylococcus aureus* and *Streptococcus pyogenes*.

Example 2

Medium S-3 seed tubes (table V) were inoculated from agar slant cultures of AB 718C-41 NNRL 18085. Seed tubes were incubated on a rotary shaker at 30° C. for 96 hr. Five percent inoculum from the first passage seed tubes was transferred to medium S-3 see flasks (table V) which were incubated on a rotary shaker at 30° for 72 hr. Five percent inoculum from the second passage seed flasks was then used to inoculate a New Brunswick 150 liter fermentor. Medium and conditions were as follows:

Fermentor Medium: 6B1 (see example 1)
Fermentor Volume: 60 liters
Antifoams: .01% XFO 371 Ivanhoe Chemical Co. Mundelein, IL
Fermentor Blade Angle: 90°
Sterilization: 1 hr., 121° C., 15–16 psi
Incubation Temperature: 30° C.
Fermentor Air Rate: 0.7 volume/volume/minute
Fermentor Agitation: 200 rpm The fermentor was incubated for 5 days and then harvested. The supernatant fermentation broth was active against sensitive and antibiotic-resistant strains of *Staphylococcus aureus* and *Streptococcus pyogenes* in an agar diffusion inhibition zone test.

TABLE V

| ATCC 172 Slant Medium | |
|---|---|
| | gm/liter |
| glucose | 10 |
| soluble starch | 20 |

TABLE V-continued

| ATCC 172 Slant Medium | |
|---|---|
| | gm/liter |
| yeast extract | 5 |
| NZ amine | 5 |
| CaCO$_3$ | 1 |
| agar | 15 |

Add distilled water to 1.0 liter
Adjust pH to between 7.0 and 7.3

| S-3 Seed Medium | |
|---|---|
| glucose monohydrate | 1 |
| starch, Staclipse JUB (made by A. E. Staley, Decatur, IL) | 24 |
| yeast extract (made by Difco Laboratories, Detroit, MI) | 5 |
| tryptone (made by Difco Laboratories, Detroit, MI) | 5 |
| beef extract (made by Inolex Chemical Co., Chicago, IL) | 3 |
| CaCO$_3$ | 4 |

Add distilled water to 1.0 liter
Adjust pH to 7.3

Volume/seed tube: 10 ml/25×150 mm pyrex tube closed with stainless steel caps
Volume/seed flasks: 100 ml/500 ml Erlenmeyer flask with rayon plugs
Sterilization: 30 min., 121° C., 15–16 psi Example 3

Whole broth (20 liters) was adjusted to pH=7 with dilute HCl, then centrifuged and filtered through filter paper to remove the mycelial cake. The filtered broth was extracted three times with ethyl acetate (3×10 liters). Ethyl acetate extracts were combined, dryed over sodium sulfate, and concentrated under vacuum to an oily residue. The residue was chromatographed on a Sephadex LH-20 ® column eluted with CH$_2$Cl$_2$/MeOH 2:1. Active fractions were pooled and subjected to counter-current chromatography on an Ito multi-layer coil planet centrifuge ® employing a CCl$_4$/CHCl$_3$/MeOH/H$_2$O 7:3:7:3 solvent system (lower phase stationary). Three active bands from the CPC were separately chromatographed on Sephadex LH-20 ® eluted with CH$_2$Cl$_2$/MeOH 2:1 to yield 3 pure components; tiacumicins A (10 mg), B (35 mg) and C (24 mg). The mycelial mass was soaked twice in acetone (2×1 liter) which was then filtered off, and the filtrate was evaporated to an aqueous concentrate. This aqueous suspension was diluted with distilled water to a volume of 2 liters and extracted 3 times with ethyl acetate (3×1 liter). Ethyl acetate extracts were combined, dryed over sodium sulfate and concentrated to an oily residue. The residue was triturated twice with hexane (2×1 liter), and the hexane layers were discarded leaving a clear oily residue. This residue was treated similarly to the filtered broth ethyl acetate extract and yielded additional material of tiacumicins B and C.

Example 4

Whole broth (4500 liters) was adjusted to pH 7 with H$_2$SO$_4$ then diluted to a volume of 5,900 liters with fresh water. The mycelial mass was removed by passing the diluted broth through a DeLarol 207 centrifuge. The filtered broth was diluted with acetone (1600 liters) and extracted three times with ethyl acetate (1700 liters, 1200 liters, and 700 liters). The extracts were combined and concentrated under reduced pressure to an oily residue. The residue was partitioned between CHCl$_3$/MeOH/H$_2$O (15 liters of each), and the upper layer was discarded. The lower layer was concentrated to an oil, and the CHCl$_3$/MeOH/H$_2$O partitioning repeated an additional two times. The final lower layer residue was partitioned between MeOH and hexane (6 liters of each). The upper layer was discarded, and the lower layer concentrated to a residue. This residue was triturated with hexane 4 times (4×6 liters), and the hexane was discarded. The remaining residue (200 grams), was chromatographed in 5 batches over a Sephadex LH-20 ® column (3×36 inches) eluted with CH$_2$Cl$_2$/MeOH 2:1. Active fractions from each LH-20 ® column were combined and separately subjected to flash chromatography on Baker C$_{18}$ bonded phase. C$_{18}$ columns were eluted with a step gradient ranging from H$_2$O to MeOH in 25% increments. Active fractions (eluted with 75 and 100% MeOH) were combined and concentrated by evaporation under reduced pressure followed lyophylization to yield a solid residue (10 g from each of the 5 columns). Each batch was chromatographed on a silica gel column (3×40 inches) and eluted with a step gradient of CHCl$_3$ to 50% MeOH. The active fractions from all silica gel columns were combined into two pools which were concentrated to leave 2.5 grams and 0.2 grams of white powder, respectively. The first pool was chromatographed in 10 batches on an Ito multi-layer coil planet centrifuge ® employing a CCl$_4$/CHCl$_3$/MeOH/H$_2$O 7:3:7:3 solvent system to yield pure tiacumicins B (3.82 grams), C (2.08 grams) and F (13 milligrams). The second pool was chromatographed on Baker C$_{18}$ bonded phase silica gel to yield pure tiacumicin D (7 milligrams) and tiacumicin E (20 milligrams).

The foregoing is merely illustrative of the invention and is not intended to limit the invention to the disclosed compounds. Variations and changes which are obvious to one skilled in the art are intended to be within the scope of the invention which is defined in the appended claims.

What is claimed is:
1. A compound of the formula:

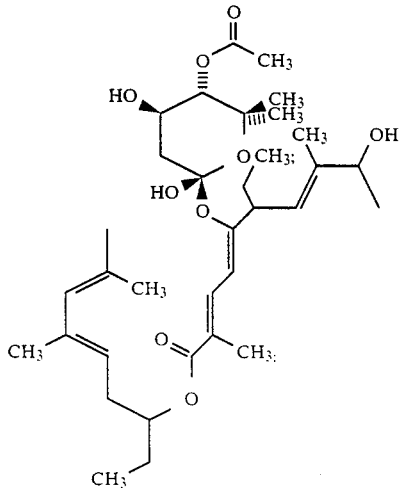

13
-continued
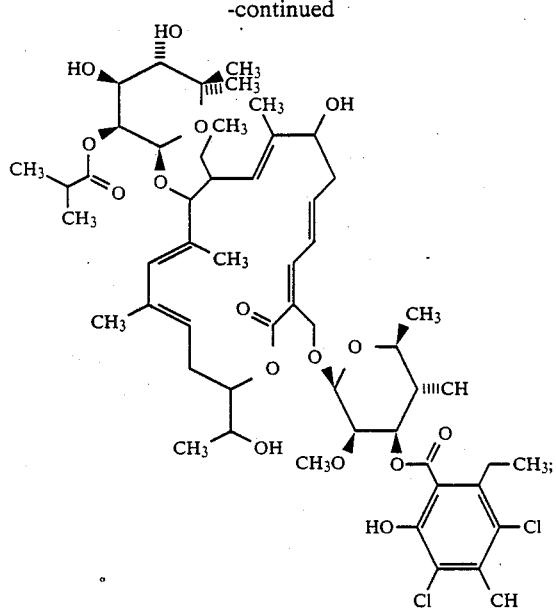
14
-continued
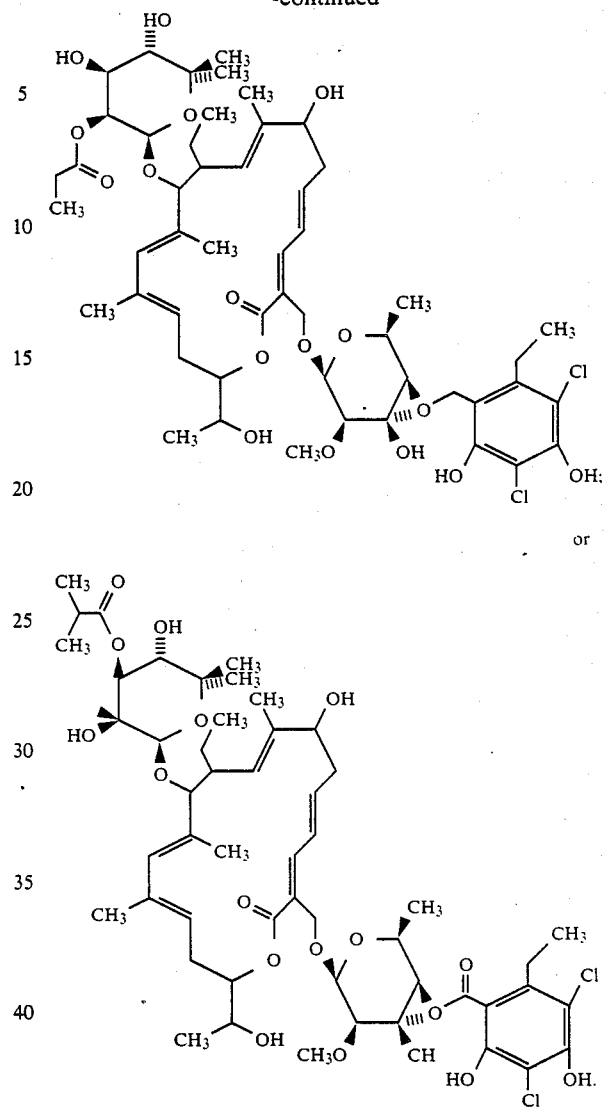
or
2. A substantially pure compound of the formula:
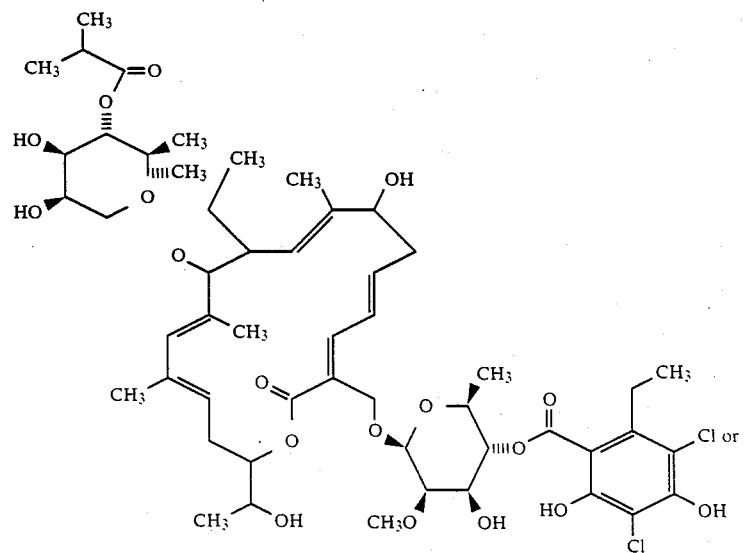
or -continued

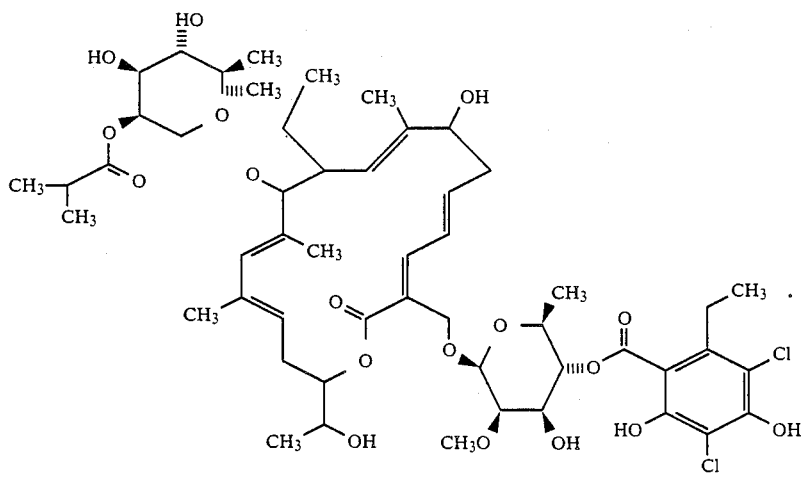

3. A process for producing a tiacumicin compound which comprises culturing a microorganism belonging to the species *Dactylosporangium aurantiacum* subsp. *hamdenensis* having the ability to produce a tiacumicin compound in a nutrient medium and accumulating a tiacumicin compound on said medium.

4. The process as recited in claim 3 wherein said microorganism is *Dactylosporangium aurantiacum* NRRL 18085.

5. The process as recited in claim 4 wherein said tiacumicin compound is isolated from said culture medium.

6. The process as recited in claim 4 wherein said microorganism is cultured at a temperature of 25° to 35° C. and a pH of 6-9.

7. A composition having antibacterial activity which comprises a clear oil, produced by culturing a microorganism belonging to the species *Dactylosporangium aurantiacum* subsp. *hamdenensis* having the ability to produce a tiacumicin compound, characterized by:
 a. a molecular weight of 604;
 b. an infrared absorption spectrum as shown in accompanying FIG. 2;
 c. an ultraviolet absorption spectrum as shown in accompanying FIG. 1; and
 d. a hydrogen nuclear magnetic resonance spectrum as shown in accompanying FIG. 3.

8. A composition having antibacterial activity which comprises a white crystalline solid, produced by culturing a microorganism belonging to the species *Dactylosporangium aurantiacum* subsp. *hamdenensis* having the ability to produce a tiacumicin compound, characterized by:
 a. a molecular weight of 1056;
 b. an ultraviolet absorption spectrum as shown in accompanying FIG. 4;
 c. an infrared absorption spectrum as shown in accompanying FIG. 5; and
 d. a hydrogen nuclear magnetic resonance spectrum as shown in accmpanying FIG. 6.

9. A composition having antibacterial activity which comprises a white crystalline solid, produced by culturing a microorganism belonging to the species *Dactylosporangium aurantiacum* subsp. *hamdenensis* having the ability to produce a tiacumicin compound, characterized by:
 a. a molecular weight of 1056;
 b. an ultraviolet absorption spectrum as shown in accompanying FIG. 7;
 c. an infrared absorption spectrum as shown in accompanying FIG. 8; and
 d. a hydrogen nuclear magnetic resonance spectrum as shown in accompanying FIG. 9.

10. A composition having antibacterial activity which comprises a white crystalline solid, produce by culturing a microorganism belonging to the species *Dactylosporangium aurantiacum* subsp. *hamdenensis* having the ability to produce a tiacumicin compound, characterized by:
 a. a molecular weight of 1056;
 b. an ultraviolet absorption spectrum as shown in accompanying FIG. 10;
 c. an infrared absorption spectrum as shown in accompanying FIG. 11; and
 d. a hydrogen nuclear magnetic resonance spectrum as shown in accompanying FIG. 12.

11. A composition having antibacterial activity which comprises a white crystalline solid, produced by culturing a microorganism belonging to the species *Dactylosporangium aurantiacum* subsp. *hamdenensis* having the ability to produce a tiacumicin compound, characterized by:
 a. a molecular weight of 1042;
 b. an ultraviolet absorption spectrum as shown in accompanying FIG. 13;
 c. an infrared absorption spectrum as shown in accompanying FIG. 14; and
 d. a hydrogen nuclear magnetic resonance spectrum as shown in accompanying FIG. 15.

12. A composition having antibacterial activity which comprises a white crystalline solid, produced by culturing a microorganism belonging to the species *Dactylosporangium aurantiacum* subsp. *hamdenensis* having the ability to produce a tiacumicin compound, characterized by:
 a. a molecular weight of 1056;
 b. an ultraviolet absorption spectrum as shown in accompanying FIG. 16;
 c. an infrared absorption spectrum as shown in accompanying FIG. 17; and
 d. a hydrogen nuclear magnetic resonance spectrum as shown in accompanying FIG. 18.

* * * * *

UNITED STATES PATENT AND TRADEMARK OFFICE
CERTIFICATE OF CORRECTION

PATENT NO. : 4,918,174

DATED : April 17, 1990

INVENTOR(S) : James B. McAlpine, Marianna Jackson, James Karwowski

It is certified that error appears in the above-identified patent and that said Letters Patent is hereby corrected as shown below:

Column 12, line 50, Structure should read as follows:

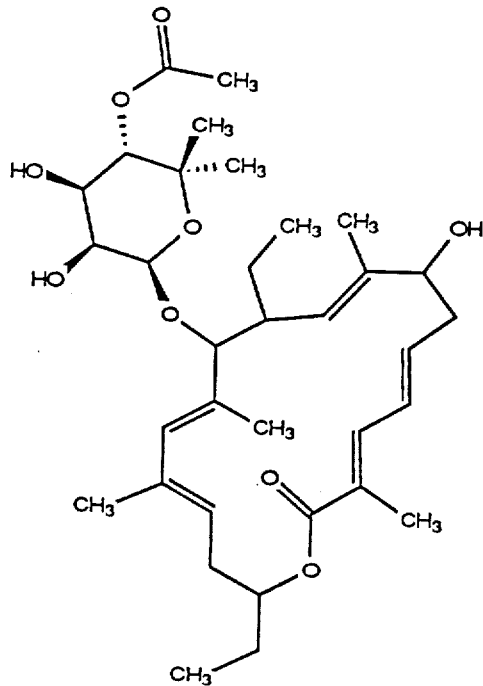

UNITED STATES PATENT AND TRADEMARK OFFICE
CERTIFICATE OF CORRECTION

PATENT NO. : 4,918,174

DATED : April 17, 1990

INVENTOR(S) : James B. McAlpine, Marianna Jackson, James Karwowski

It is certified that error appears in the above-identified patent and that said Letters Patent is hereby corrected as shown below:

Column 13, line 3, Structure should read as follows:

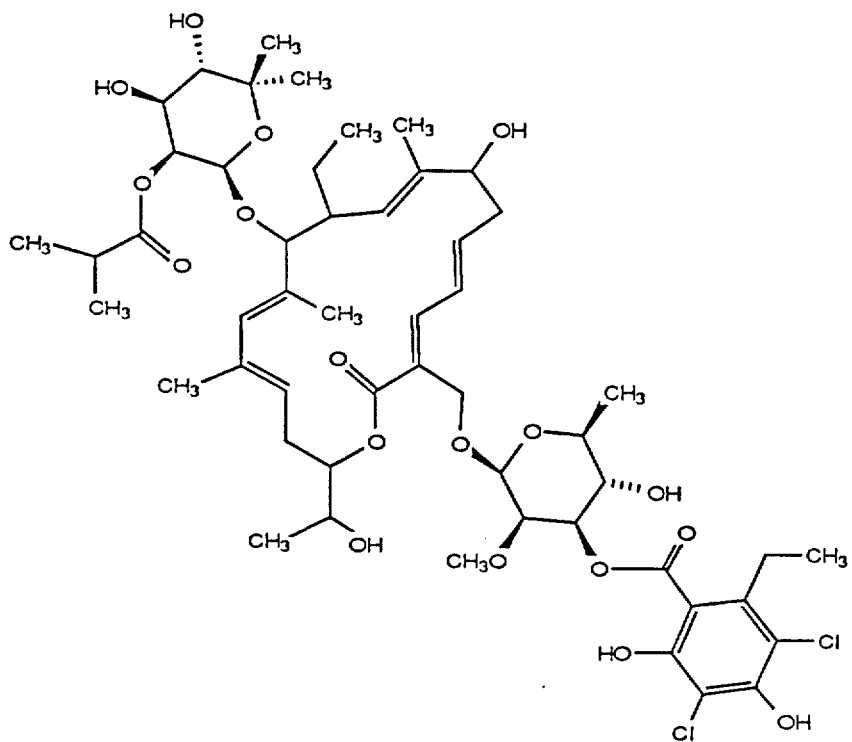

UNITED STATES PATENT AND TRADEMARK OFFICE
CERTIFICATE OF CORRECTION

PATENT NO. : 4,918,174

DATED : April 17, 1990

INVENTOR(S) : James B. McAlpine, Marianna Jackson, James Karwowski

It is certified that error appears in the above-identified patent and that said Letters Patent is hereby corrected as shown below:

Column 14, line 3, Structure should read as follows:

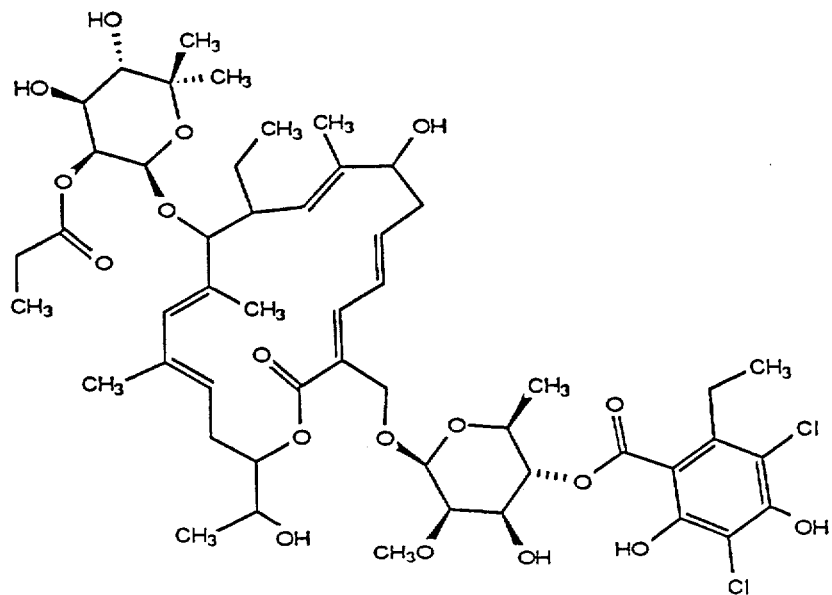

UNITED STATES PATENT AND TRADEMARK OFFICE
CERTIFICATE OF CORRECTION

PATENT NO. : 4,918,174
DATED : April 17, 1990
INVENTOR(S) : James B. McAlpine, Marianna Jackson, James Karwowski It is certified that error appears in the above-identified patent and that said Letters Patent is hereby corrected as shown below:

Column 14, line 23, Structure should read as follows:

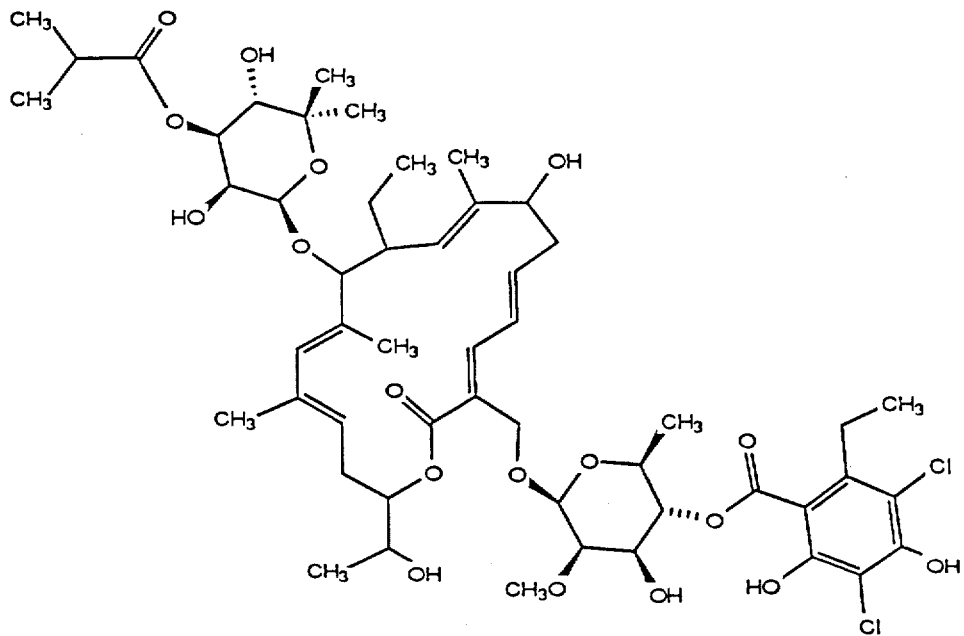

UNITED STATES PATENT AND TRADEMARK OFFICE
CERTIFICATE OF CORRECTION

PATENT NO. : 4,918,174

DATED : April 17, 1990

INVENTOR(S) : James B. McAlpine, Marianna Jackson, James Karwowski

It is certified that error appears in the above-identified patent and that said Letters Patent is hereby corrected as shown below:

Column 14, line 50, Structure should read as follows:

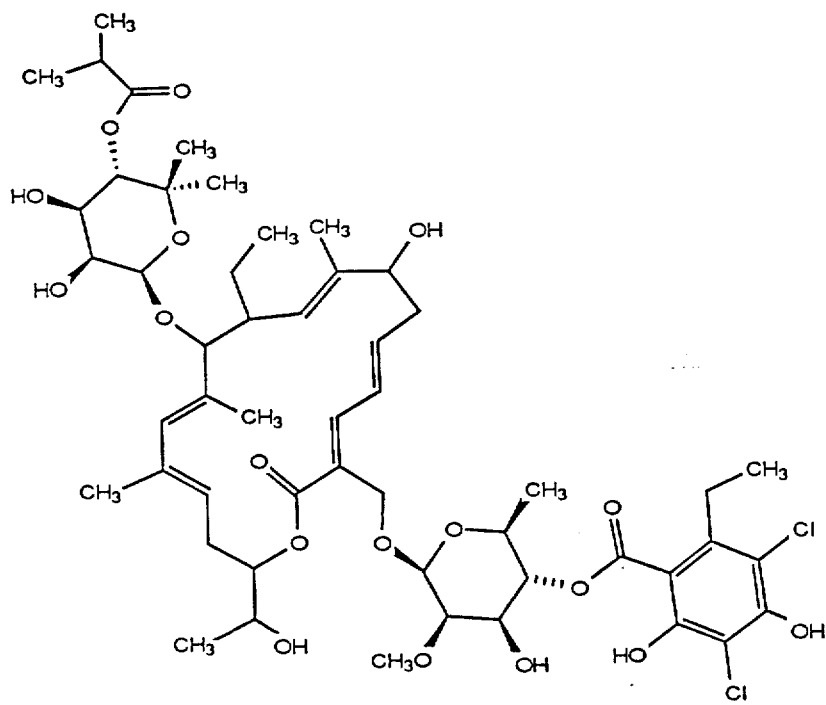

UNITED STATES PATENT AND TRADEMARK OFFICE
CERTIFICATE OF CORRECTION

PATENT NO. : 4,918,174

DATED : April 17, 1990

INVENTOR(S) : James B. McAlpine, Marianna Jackson, James Karwowski

It is certified that error appears in the above-identified patent and that said Letters Patent is hereby corrected as shown below:

Column 12, line 50, Structure should read as follows:

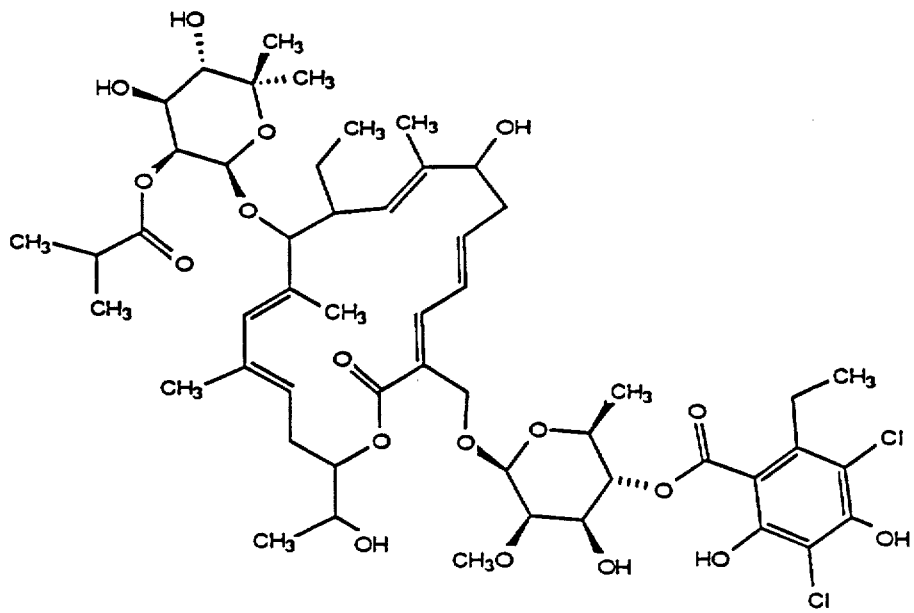

Signed and Sealed this

Thirtieth Day of April, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,918,174
DATED : April 17, 1990
INVENTOR(S) : McAlpine, et al.

It is certified that error appears in the above-identified patent and that said Letters Patent is hereby corrected as shown below:

Caption, Page 1, should identify James B. McAlpine, Marianna Jackson, James Karwowski, Robert J. Theriault, and Jill Hochlowski, as Inventors.

Signed and Sealed this

Twenty-eighth Day of May, 1991

*Attest:*

HARRY F. MANBECK, JR.

*Attesting Officer*  *Commissioner of Patents and Trademarks*